United States Patent
Efrat et al.

(10) Patent No.: US 9,394,523 B2
(45) Date of Patent: Jul. 19, 2016

(54) INDUCED PLURIPOTENT STEM CELLS DERIVED FROM HUMAN PANCREATIC BETA CELLS

(75) Inventors: Shimon Efrat, Zikhron-Yaakov (IL); Nissim Benvenisty, Jerusalem (IL)

(73) Assignees: Ramot at Tel-Aviv University Ltd., Tel-Aviv (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/818,110

(22) PCT Filed: Jul. 7, 2011

(86) PCT No.: PCT/IL2011/000543
§ 371 (c)(1),
(2), (4) Date: Feb. 21, 2013

(87) PCT Pub. No.: WO2012/025914
PCT Pub. Date: Mar. 1, 2012

(65) Prior Publication Data
US 2013/0209421 A1    Aug. 15, 2013

Related U.S. Application Data

(60) Provisional application No. 61/375,835, filed on Aug. 22, 2010.

(51) Int. Cl.
*C12N 5/00* (2006.01)
*C12N 5/071* (2010.01)
*C12N 5/074* (2010.01)

(52) U.S. Cl.
CPC ............ *C12N 5/0678* (2013.01); *C12N 5/0696* (2013.01); *C12N 2501/602* (2013.01); *C12N 2501/603* (2013.01); *C12N 2501/604* (2013.01); *C12N 2501/606* (2013.01); *C12N 2506/03* (2013.01); *C12N 2506/22* (2013.01)

(58) Field of Classification Search
CPC .................................................. C12N 2506/03
USPC ....................................................... 435/377
See application file for complete search history.

(56) References Cited

U.S. PATENT DOCUMENTS

| 2009/0191159 A1 | 7/2009 | Sakurada et al. |
| 2009/0299763 A1 | 12/2009 | Sakurada |
| 2009/0324559 A1 | 12/2009 | Sakurada et al. |

FOREIGN PATENT DOCUMENTS

| WO | WO 2009/137844 | 11/2009 |
| WO | WO 2010/056808 | 5/2010 |
| WO | WO 2010/091241 | 8/2010 |
| WO | WO 2012/025914 | 3/2012 |

OTHER PUBLICATIONS

Tateishi et al. cited on IDS Feb. 24, 2013.*
Stadtfeld et al. (2008, Curr. Biol., vol. 18(12), pp. 1-11).*
Ross et al. (2010, Cell and Development, vol. 19 (8), pp. 1221-1229).*
D'Amour et al. (2006, Nature Biotechnology, vol. 24(11), pp. 1392-1401).*
Chakrabarti et al. (2002, JBC, vol. 277(15), pp. 13286-13293).*
Ouziel-Yahalom et al. (2006, Biochem. Biophys. Res. Comm., vol. 341, pp. 291-298).*
Weingberg et al. (2007, Diabetes, vol. 56, pp. 1299-1304).*
Planello et al. (2014, Cell Regeneration, vol. 3(4), pp. 1-14).*
Nissenbaum et al., 2013, Stem Cell Reports, vol. 1, pp. 509-517.*
Ivashchenko et al. (2013, Am. J. Physiol. Heart Circ., vol. 305, pp. H913-H922).*
International Search Report and the Written Opinion Dated Nov. 23, 2011 From the International Searching Authority Re. Application No. PCT/IL2011/000543.
Kim et al. "Epigenetic Memory in Induced Pluripotent Stem Cells", Nature, XP009149206, 467(7313): 285-292, Jul. 19, 2010. Abstract, Figs. 1-4.
Liew "Generation of Insulin-Producing Cells From Pluripotent Stem Cells: From the Selection of Cell Sources to the Optimization of Protocols", The Review of Diabetic Studies, XP009153056, 7(2): 82-92, Jul. 2010.
McKnight et al. "Deconstructing Pancreas Development to Reconstruct Human Islet From Pluripotent Stem Cells", Cell Stem Cell, XP009153055, 6(4): 300-308, Apr. 2010. Fig.1, Tables 1, 2.
Russ et al. "In Vitro Proliferation of Cells Derived From Adult Human Beta-Cells Revealed by Cell-Lineage Tracing", Diabetes, XP009101475, 57(6): 1575-1583, Jun. 1, 2008. p. 1575, Col. 2, Para 2—p. 1576.
Stadtfeld et al. "Reprogramming of Pancreatic β Cells Into Induced Pluripotent Stem Cells", Current Biology, 18:890-894, Jun. 24, 2008.
Tateishi et al. "Generation of Insulin-Secreting Islet Clusters From Human Skin Fibroblasts", The Journal of Biological Chemistry, XP009147429, 283(46): 31601-31607, Nov. 14, 2008. Figs.1-4.
International Preliminary Report on Patentability Dated Mar. 7, 2013 From the International Bureau of WIPO Re. Application No. PCT/IL2011/000543.
Search Report and Written Opinion Dated Nov. 25, 2013 From the Intellectual Property Office of Singapore Issued by the Austrian Patent Office Re. Application No. 201301069-9.

(Continued)

*Primary Examiner* — Anoop Singh
*Assistant Examiner* — David A Montanari

(57) ABSTRACT

A method of generating pluripotent stem cells is described. The method comprises:
(a) expanding human pancreatic beta cells; and subsequently
(b) generating induced pluripotent stem (iPS) cells from the human pancreatic beta cells.

Methods of redifferentiating the iPS cells into particular cell types are also disclosed. Uses of the cell populations are also described.

13 Claims, 18 Drawing Sheets
(15 of 18 Drawing Sheet(s) Filed in Color)

(56) References Cited

OTHER PUBLICATIONS

Bar-Nur et al. "Epigenetic Memory and Preferential Lineage-Specific Differentiation in Induced Pluripotent Stem Cells Derived From Human Pancreatic Islet Beta Cells", Cell Stem Cell, 9(1): 17-23, Jul. 8, 2011. Abstract.

Maehr et al. "Generation of Pluripotent Stem Cells From Patients With Type 1 Diabetes", Proc. Natl. Acad. Sci. USA, PNAS Early Edition, 106(37): 15768-15773, Sep. 2009. Abstract.

Zhang et al. "Highly Efficient Differentiation of Human ES Cells and iPS Cells Into Mature Pancreatic Insulin-Producing Cells", Cell Research, 19(4): 429-438, Apr. 2009. Abstract.

Zhou et al. "In Vivo Reprogramming of Adult Pancreatic Exocrine Cells to Beta-Cells", Nature, 455(7213): 627-632, Oct. 2008. Abstract.

\* cited by examiner

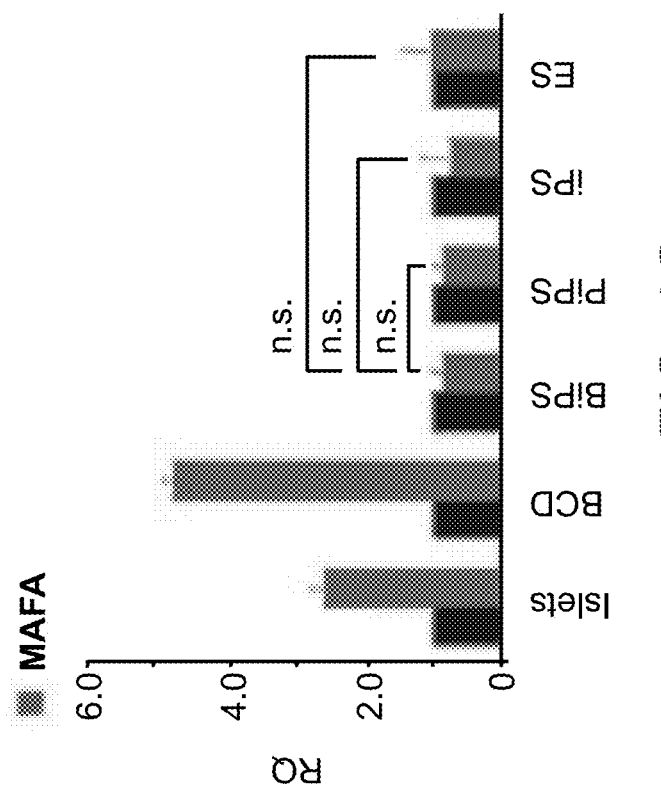
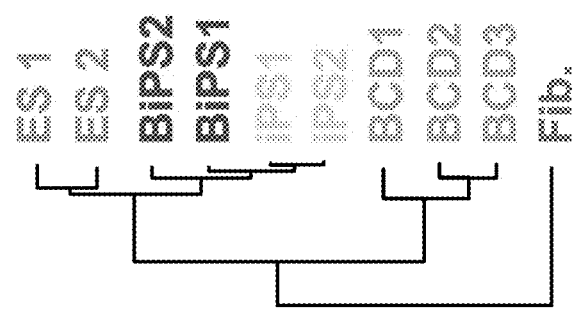
FIG. 1G
FIG. 1H

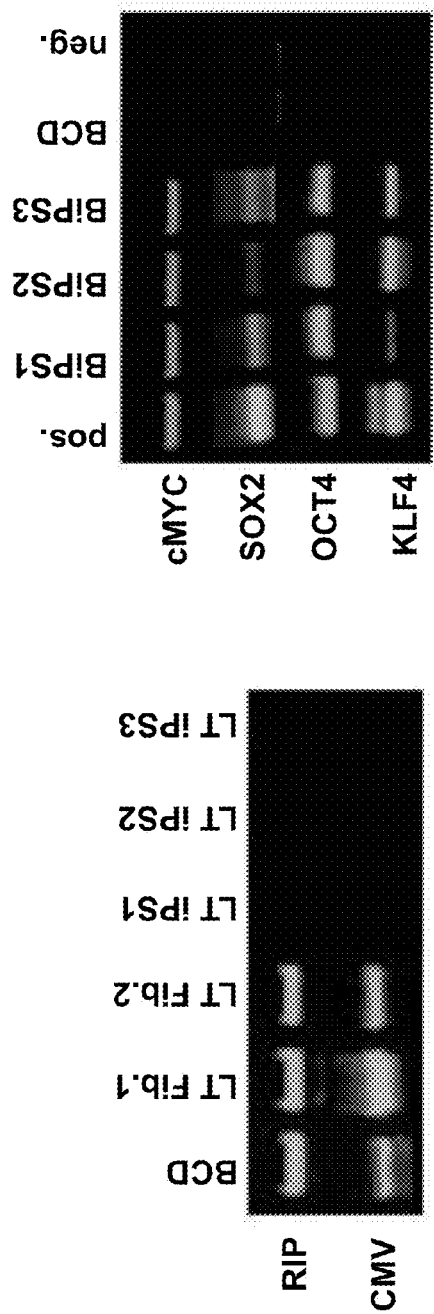
FIG. 3E
FIG. 3D
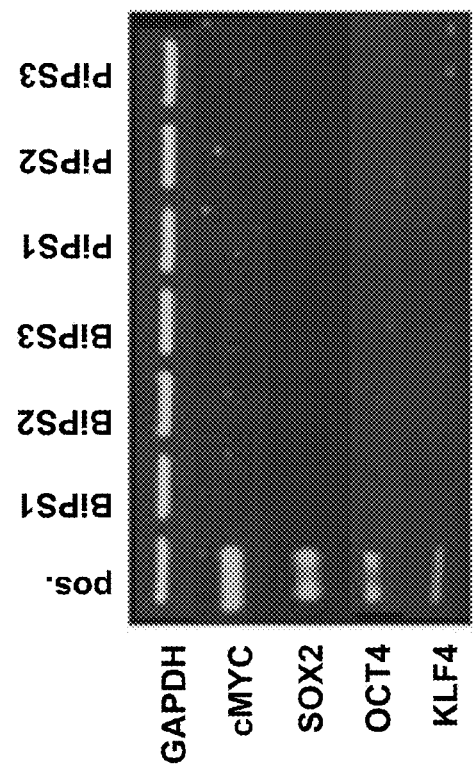
FIG. 3F

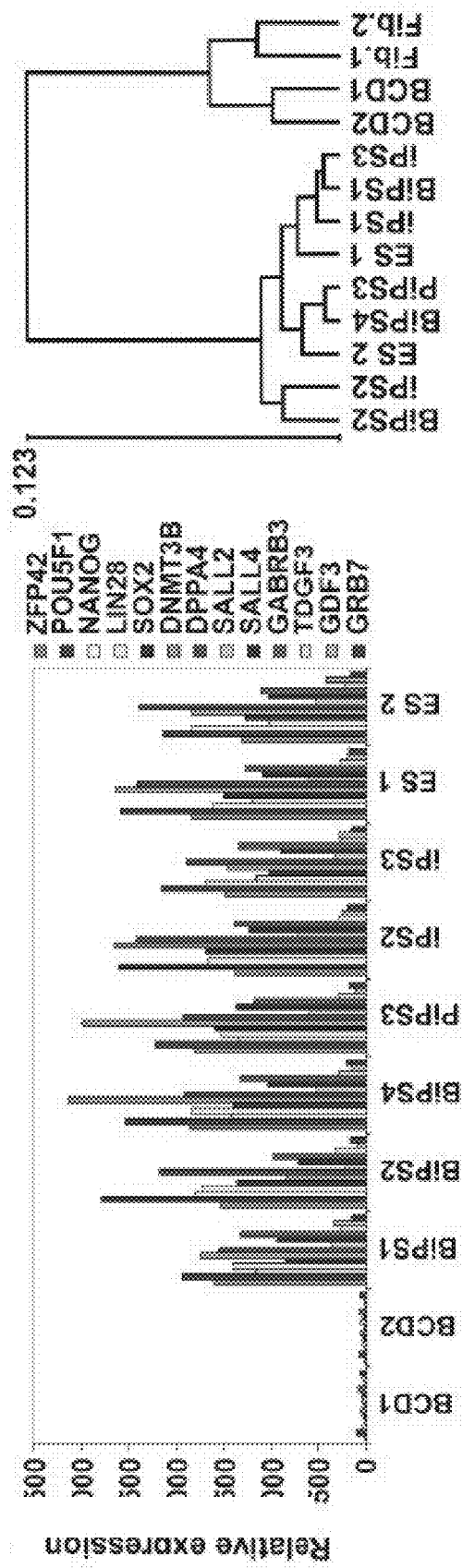

INDUCED PLURIPOTENT STEM CELLS DERIVED FROM HUMAN PANCREATIC BETA CELLS

RELATED APPLICATIONS

This application is a National Phase of PCT Patent Application No. PCT/IL2011/000543 having International filing date of Jul. 7, 2011, which claims the benefit of priority under 35 USC §119(e) of U.S. Provisional Patent Application No. 61/375,835 filed on Aug. 22, 2010. The contents of the above applications are all incorporated by reference as if fully set forth herein in their entirety.

SEQUENCE LISTING STATEMENT

The ASCII file, entitled 55751SequenceListing.txt, created on Jan. 30, 2013, comprising 7,007 bytes, submitted concurrently with the filing of this application is incorporated herein by reference

FIELD AND BACKGROUND OF THE INVENTION

The present invention, in some embodiments thereof, relates to induced pluripotent stem cells (iPS) derived from human pancreatic beta cells, uses thereof and methods of obtaining same.

Type I diabetes is caused by the autoimmune destruction of the pancreatic islet insulin-producing beta cells. Insulin administration does not prevent the long-term complications of the disease, since the optimal insulin dosage is difficult to adjust. Replacement of the damaged cells with regulated insulin-producing cells is considered the ultimate cure for type 1 diabetes. Pancreas transplantation has been successful but is severely limited by the shortage of donors. With the development of new islet isolation and immunosuppression procedures, significant success has been reported using islets from 2-3 donors per recipient [Shapiro A M, Lakey J R, Ryan E A et al. New Engl J Med 2000; 343:230-238]. U.S. Patent Application No. 20080014182 teaches methods of expanding human pancreatic beta cells and subsequent redifferentiation thereof.

However, there remains an urgent need for developing alternatives to human pancreas donors, namely abundant sources of cultured human pancreatic β cells for transplantation.

One alternative to forced expansion of post-mitotic pancreatic β cells is the induction of differentiation of stem/progenitor cells into insulin-producing cells.

Human embryonic stem (ES) cells, derived from the inner cell mass of blastocyst-stage embryos, are capable of unlimited proliferation in vitro while maintaining their potential to differentiate into cells from the three embryonic germ layers. The directed differentiation of embryonic stem cells has generated cells that only produce low amounts of insulin, compared to β cells, and their potential use in transplantation has met with ethical objections.

Human induced pluripotent stem (iPS) cells have been recently generated from human somatic fibroblasts by expression of defined transcription factors. iPS cells have also been generated from other human cell types, including $CD34^+$ cells from peripheral blood, keratinocytes and neural stem cells.

U.S. Patent Application Nos. 20090047263 and 20110014164 teach generation of human iPS cells from, amongst many other somatic cells, pancreatic cells.

Human iPS cells fulfill all current criteria of true human pluripotent stem cells and may offer an alternative cell source for cell replacement therapy and for in-vitro models of genetic diseases. Although human iPS cells were shown to be similar to human ES cells, as judged by expression of pluripotency genes and their ability to generate embryoid bodies (EBs) and teratomas, mounting evidence suggests that iPS cells differ from ES cells in gene expression profiles, persistence of donor-cell gene expression, differentiation abilities, tumorigenicity, stability of imprinted gene expression, and disease modeling. Recently, it has been shown that following the reprogramming of mouse iPS cells, an epigenetic memory is inherited from the parental cell [Kim, K et al. Nature. 467, 285-290 (2010); Polo J M et al., Nat. Biotechnol. 28(8), 848-855 (2010)].

Some emerging works also show a unique DNA methylation signature that is derived from a parental human cell following reprogramming [Doi A., et al. Nat Genet. 41 1350-1353 (2009); Kim Ey., et al. Cell reprogram. 12 627-639 (2010); Lister et al. Nature 471, 68-73 (2011)].

Stadtfeld et al., [Current Biology 18, 890-894, 2008] teaches generation of iPS cells derived from mouse pancreatic beta cells in order to establish that fully differentiated cells may be used to generate iPS cells.

Other background art includes Eminli, S. et al. Nat. Genet. 41, 968-976 (2009), Kim et al., Nature. 467, 285-290 (2010); and Polo et al., Nat. Biotechnol. 28(8), 848-855 (2010).

SUMMARY OF THE INVENTION

According to an aspect of some embodiments of the present invention there is provided a method of generating pluripotent stem cells, comprising:

(a) expanding human pancreatic beta cells; and subsequently (b) generating induced pluripotent stem (iPS) cells from the human pancreatic beta cells.

According to an aspect of some embodiments of the present invention there is provided a method of generating cells useful for treating Diabetes, comprising:

(a) expanding human pancreatic beta cells;

(b) generating induced pluripotent stem (iPS) cells from the human pancreatic beta cells; and (c) differentiating the induced pluripotent stem cells towards a pancreatic lineage, thereby generating cells useful for treating Diabetes.

According to an aspect of some embodiments of the present invention there is provided a method of generating cells useful for treating a disease associated with cellular malfunction, the method comprising:

(a) generating induced pluripotent stem cells from human somatic cells, the human somatic cells being selected according to the cells which have mal-functioned in the disease; and (b) redifferentiating the induced pluripotent stem cells towards an original somatic lineage of the induced pluripotent stem cells, thereby generating cells useful for treating a disease associated with cellular malfunction.

According to an aspect of some embodiments of the present invention there is provided a method of generating cells useful for treating a disease associated with cellular malfunction, the method comprising:

(a) expanding human somatic cells; and subsequently (b) generating induced pluripotent stem cells from the human somatic cells, the human somatic cells being selected according to the cells which have mal-functioned in the disease; and (c) redifferentiating the induced pluripotent stem cells towards an original somatic lineage of the induced pluripotent stem cells, thereby generating cells useful for treating a disease associated with cellular malfunction.

According to an aspect of some embodiments of the present invention there is provided a method of generating cells useful for treating Diabetes, comprising:

(a) generating induced pluripotent stem (iPS) cells from human pancreatic beta cells; and (b) differentiating the induced pluripotent stem cells towards a pancreatic lineage, thereby generating cells useful for treating Diabetes.

According to an aspect of some embodiments of the present invention there is provided an isolated population of cells generated according to the methods described herein.

According to an aspect of some embodiments of the present invention there is provided a pharmaceutical composition comprising the isolated populations of cells of the present invention.

According to an aspect of some embodiments of the present invention there is provided a method of treating Diabetes in a subject in need thereof comprising transplanting a therapeutically effective amount of the isolated population of cells of the present invention into the subject, thereby treating Diabetes in the subject.

According to an aspect of some embodiments of the present invention there is provided a use of the isolated population of cells of any of the present invention for the treatment of a disease associated with cellular malfunction.

According to some embodiments of the invention, the expanding is effected in a medium comprising CMRL-1066.

According to some embodiments of the invention, the expanding is effected for 3-16 weeks.

According to some embodiments of the invention, the generating induced pluripotent stem cells is effected by expressing in the human pancreatic beta cells at least one dedifferentiating factor, wherein the dedifferentiating factor is selected from the group consisting of Klf4, c-Myc, Oct3/4, Sox2, Nanog, and Lin28.

According to some embodiments of the invention, the generating induced pluripotent stem cells is effected by expressing in the human pancreatic beta cells Oct3/4, Sox2, Klf4 and c-Myc.

According to some embodiments of the invention, the expressing is effected by introducing into the human pancreatic beta cells a DNA molecule encoding the at least one dedifferentiating factor.

According to some embodiments of the invention, the expressing is effected by introducing into the human pancreatic beta cells an RNA molecule encoding the at least one dedifferentiating factor.

According to some embodiments of the invention, the human pancreatic beta cells are a homogeneous population of human pancreatic beta cells.

According to some embodiments of the invention, the human pancreatic beta cells are comprised in a mixed population of pancreatic cells.

According to some embodiments of the invention, the method further comprises selecting the iPS cells derived from human pancreatic beta cells following step (b).

According to some embodiments of the invention, the selecting is effected by analyzing a chromatin structure of a promoter of an insulin or PDX-1 gene in the iPS cells.

According to some embodiments of the invention, the selecting is effected by analyzing a DNA methylation status of a pancreatic beta cell specific gene.

According to some embodiments of the invention, the pancreatic beta cell specific gene is selected from the group consisting of insulin, MT1H, WDR52, NUCB1, cd40 and PDX-1 and ZNF4A.

According to some embodiments of the invention, the selecting is effected by genetic labeling.

According to some embodiments of the invention, the differentiating the induced pluripotent stem cells towards a pancreatic lineage is effected by differentiating the induced pluripotent stem cells into definitive endoderm and subsequently differentiating the definitive endoderm cells into pancreatic progenitor cells.

According to some embodiments of the invention, the differentiating the induced pluripotent stem cells into definitive endoderm is effected by culturing the induced pluripotent stem cells in a medium comprising an agent selected from the group consisting of activin A, IDE1 and IDE2.

According to some embodiments of the invention, the differentiating the definitive endoderm into pancreatic progenitor cells is effected by culturing the definitive endoderm in a medium comprising an agent selected from the group consisting of keratinocyte growth factor (KGF), retinoic acid, epidermal growth factor (EGF), nicotinamide, fibroblast growth factor (FGF), insulin like growth factor (IGF), HGF and noggin.

According to some embodiments of the invention, the differentiating the definitive endoderm into pancreatic progenitor cells is effected by culturing the definitive endoderm in a differentiating factor selected from the group consisting of keratinocyte growth factor (KGF), retinoic acid and noggin.

According to some embodiments of the invention, the disease is Diabetes, the generating iPS cells is effected from human pancreatic beta cells.

According to some embodiments of the invention, the human somatic cells are a homogeneous population of human somatic cells.

According to some embodiments of the invention, the human somatic cells are comprised in a heterogeneous population of human somatic cells.

According to some embodiments of the invention, the method further comprises isolating iPS cells which have been dedifferentiated from the selected somatic cells.

According to some embodiments of the invention, the isolating is effected by analyzing a chromatin structure of a promoter of a specific gene of the somatic cells in the iPS cells.

According to some embodiments of the invention, the isolating is effected by analyzing a DNA methylation status of a specific gene of the somatic cells in the iPS cells.

According to some embodiments of the invention, the cells comprise at least two exogenous expression constructs, wherein a first expression construct comprises a polynucleotide encoding a Cre recombinase polypeptide operatively linked to a B cell specific promoter; and wherein a second expression construct comprises a first polynucleotide encoding a first detectable moiety operatively linked to a constitutive promoter, the first polynucleotide being flanked by LoxP polynucleotides, the second expression construct further comprising a second polynucleotide encoding a second detectable moiety, the second polynucleotide being positioned 3' to the first polynucleotide.

According to some embodiments of the invention, the disease is Diabetes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C:
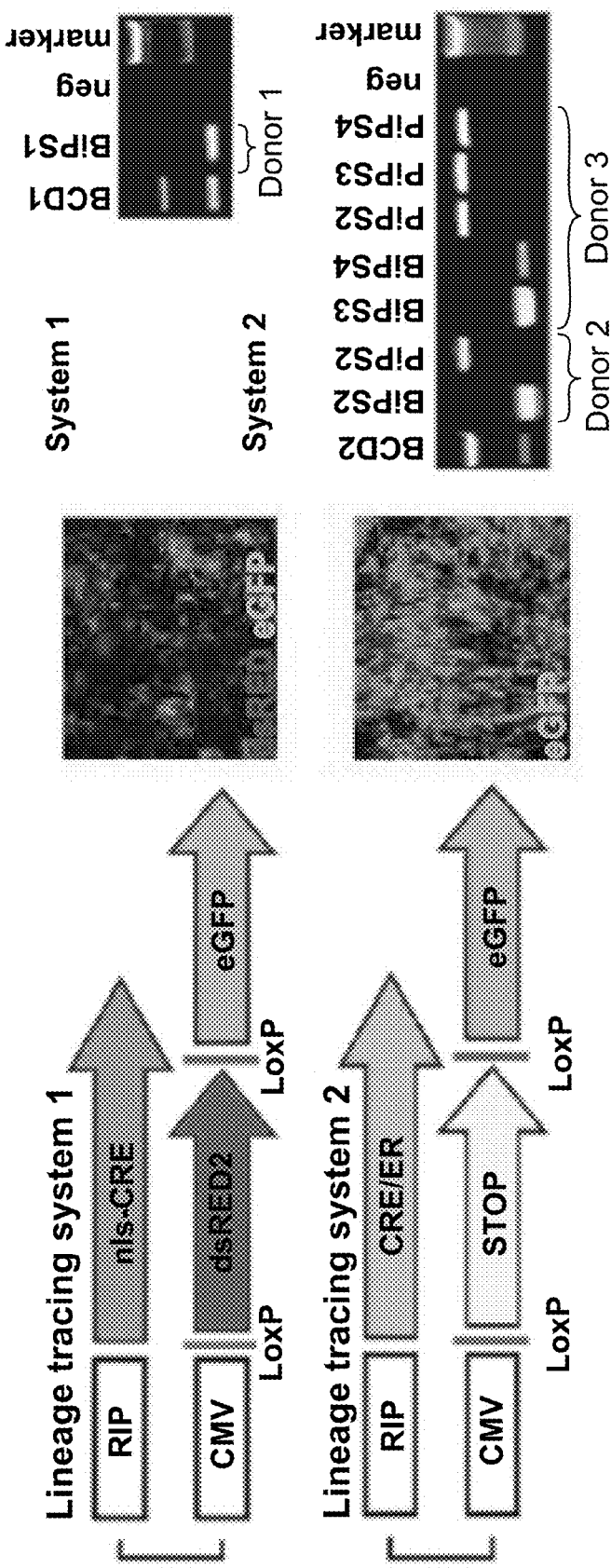

FIGS. 1A-J illustrate genetic labeling of human beta cells, generation of BiPS cell clones and epigenetic memory in BiPS cells. A: Schematic representation of two dual lentiviral lineage-tracing systems for specific labeling of human beta cells. (RIP=rat insulin promoter, NLS=nuclear localization signal, cre=cre recombinase, dsRED2=red fluorescent protein 2, GFP=green fluorescent protein, CMV=cytomegalovirus promoter, ER=estrogen receptor inducible promoter); B: Representative images of GFP$^+$ Beta cell derived (BCD) cells at passage 3 generated with each labeling system. Note that cells labeled with system 2 were enriched by FACS sorting. C: PCR analysis of DNA from lineage-traced islet cells containing labeled BCD, beta cell derived induced pluripotent cells (BiPS) and non-beta pancreatic derived pluripotent (PiPS) cells, using primers spanning the floxed DNA fragment of each reporter vector. Both the original and the recombined DNA fragments are seen in the parental BCD cells (although in different ratios in the two systems), while the 4 PiPS cells show the original fragment, and the 4 BiPS cell clones show only the recombined DNA fragment (lower band). D: qPCR analysis of insulin, PDX1 and MAFA expression in islet, BCD, and undifferentiated BiPS, PiPS, iPS and ES cells. E: Chromatin immunoprecipitation (ChIP) analysis of histone H3-tail acetylation in fresh islet cells in comparison to sorted GFP$^+$ BCD cells and non-labeled islet cells after 7-11 weeks in culture. Note that the unlabeled fraction contains unlabeled BCD cells. qPCR analysis was performed on bound and input DNA with primers recognizing the promoter regions of insulin (−275), PDX1 or MAFA. Values are mean±SD (n=3-5 donors) and are normalized to crystallin. F-G: ChIP analysis of histone H3-tail acetylation in Islet, BCD, BiPS, PiPS, iPS, and ES cells at promoters of key beta-cell genes. qPCR was performed on bound and input DNA with primers recognizing the insulin locus at positions −275, +5, and +1318 from the transcription start site, and PDX1 or MAFA promoters. Values are mean±SE (n=3-4 cell lines) and are normalized to crystallin. n.s.: not significant. H: Hierarchical clustering of BiPS, iPS, ES, BCD and fibroblast cells using Illumina's Infinium HumanMethylation arrays I: DNA methylation analysis of specific genes in somatic and pluripotent stem cells. The status of DNA methylation was determined using Illumina's Infinium HumanMethylation arrays. Shown are I—pluripotency-related genes that underwent demethylation following reprogramming; II—somatic-related genes that underwent methylation following reprogramming; III—islet expressed genes that are hypomethylated in BCD cells and remain hypomethylated in BiPS cells, relative to other cell types (RM=Relative methylation). J: Pyrosequencing analysis of DNA methylation at the PDX1 promoter on 13 CpG island positions in BiPS, compared with iPS cells. *p<0.05 in BiPS vs. iPS cells. The color bar label "High" refers to >68% methylation, while "Low" indicates no detectable methylation at the respective position.

FIGS. 2A-F illustrate skewed differentiation of BiPS cells into insulin-producing cells. A: Expression levels of insulin, PDX1 and FOXA2 transcripts in EBs at 20d analyzed by qPCR. Data represent mean of 4 BiPS cell lines, 3 PiPS cell lines, 5 iPS cell lines, and 3 ES cell lines. Values are mean±SE, compared to EBs from ES cells (RQ=1). B: qPCR analysis of insulin, PDX1 and FOXA2 transcripts in teratomas at 30d derived from BiPS, PiPS, iPS, and ES cells. Data represent biological repeats of 3 BiPS cell lines, 3 PiPS cell lines, 4 iPS cell lines, and 3 ES cell lines. Values are mean±SE, compared to teratomas from ES cells (RQ=1). C: Immunofluorescence analysis of insulin and C-peptide in islet cells, and EBs at 20d derived from ES and BiPS cells. The C-peptide antibody used is human specific. Nuclei were stained blue with DAPI. Bar=20 µm. Only a small number of insulin-positive areas were detected in EBs derived from BiPS cells, however none were seen in EBs derived from ES cells. D-F: Differentiation induced with the protocol of Kroon et al. (Nat. Biotechnol. 26, 443-452 (2008)). D: Serum human C-peptide levels following glucose challenge in mice transplanted with ES or BiPS cell-derived endocrine progenitors at indicated time points post-transplantation, compared with sham controls. Values are mean±SE (n=8 mice in each group). The assay sensitivity is 1.5 pmol/L. E: qPCR analysis of pancreatic gene expression in BiPS1 and BiPS2 cell-derived grafts, in comparison with ES cell-derived grafts. ΔCt is normalized to GAPDH. Values are mean±SE (n=3 mice in each group). F: Immunofluorescence analysis of C-peptide in a BiPS cell-derived graft removed 6 weeks post-transplantation. Nuclei were stained blue with DAPI. Bar=20 µm.

FIGS. 3A-I illustrate generation and characterization of the BiPS and PiPS cell lines. A: Brightfield (left panels) and fluorescence (right panels) micrographs showing the appearance of a BiPS cell colony (dotted line) at the indicated time points following infection with viruses encoding for the four reprogramming factors. The BiPS cell colony at day 21 acquired a typical ES cell-like morphology distinct from that of BCD cells. Note that GFP expression diminished, probably due to CMV promoter inactivation in the pluripotent stage. B: PCR analysis of DNA from individual cell lines using primer of RIP-Cre/ER gene in BiPS and PiPS cell lines used in the study. This analysis, together with the data shown in FIG. 1C, confirms that the PiPS cell clones did not undergo recombination, although they had acquired both labeling constructs, thus confirming their non-beta cell origin. Positive control: plasmid DNA. Negative control: uninfected islet cells. C: Lineage traced foreskin fibroblasts (left) and iPS cell derived from them (right) are not positive for GFP expression, indicating that the labeling system is specific and not affected by the reprogramming process. D: PCR analysis of DNA from lineage-traced foreskin fibroblast or iPS cells derived from them using primers spanning the floxed DNA fragment of each reporter vector. Both cell types show the original fragment, and the non-recombined fragment, indicating that no recombination had occurred following reprogramming. E: Genomic DNA PCR analysis of retroviral transgenes in established BiPS cell clones and in BCD. pos.: fibroblasts 7 days after transduction with the 4 vectors, shown to express the transgenes mRNA. neg.: no-template control. F: PCR analysis of retroviral transgene expression in established BiPS and PiPS cell clones, in comparison to fibroblasts 7 days after transduction with the 4 vectors (pos.). G: qRT-PCR analysis of endogenous pluripotency gene expression in BCD1 cells compared to 3 BiPS cell lines, 4 PiPS cell lines, 2 fibroblast iPS cell lines, and one ES cell lines. Results were normalized to UBC. H: Immunofluorescence analysis of pluripotency factors in BiPS and PiPS cell lines. AP, alkaline phosphatase activity. I: .BiPS cells exhibit a normal diploid karyotype of 46XY (BiPS1) and 46XX (BiPS2) chromosomes.

FIGS. 4A-H illustrate global gene expression in BiPS cell clones, differentiation into cells of all three embryonic germ layers in vitro and in vivo and directed differentiation of BiPS into endocrine progenitor cells.
A: BiPS cells express all the pluripotency genes analyzed at levels comparable to those of PiPS, iPS, and ES cells, while the parental BCD cells do not express them. B: Hierarchical clustering of ES, iPS, PiPS, and BiPS cells, as well as two parental BCD cell populations, and two parental fibroblast populations. C: Scatter plot analysis of BiPS cell clones vs. their parental BCD cell populations, ES, iPS, and PiPS cells. Bottom panel shows scatter plot analysis of ES and iPS cell clones according to Kroon et al., Nat. Biotechnol. 26, 443-452 (2008). D: In-vitro differentiation of BiPS cells. a: Floating BiPS cell-derived EBs at day 8. b-f: Immunofluorescence analysis of BiPS cells at day 16 of differentiation for markers of the three embryonic germ layers. b: FOXA2 (endoderm), c: alpha-fetoprotein (AFP) (endoderm), d: cardiac-fetal actin (ACTC1) (mesoderm), e: desmin (mesoderm), f: NCAM1 (ectoderm). Bar=20 µm. E: qRT-PCR analysis of representative markers from the three embryonic germ layers in undifferentiated BiPS cell clones in comparison to EBs differentiated from them: AFP (endoderm), Albumin (ALB, endoderm), CD34 (mesoderm), SCL (mesoderm), desmin (mesoderm), and nestin (ectoderm). Results were normalized to GAPDH. F: In-vivo differentiation of BiPS and PiPS cell lines: Histological sections of BiPS cell-derived or PiPS cell derived teratomas display differentiated structures of all three embryonic germ layers, including gut-like epithelium (endoderm), adipose tissue, muscle and cartilage (mesoderm), and rosette-like structures (ectoderm). Bar=20 µm. G: qPCR analysis of beta-cell-specific gene expression in BiPS cell-derived endocrine progenitors on day 12 of the Kroon protocol. Values are mean±SE (n=6-11 different experiments), in comparison to untreated BiPS cells (RQ=1), normalized to the GAPDH gene. H: Immunofluorescence analysis of PDX1 expression in endocrine progenitor cells derived from BiPS cells on day 12 of the protocol. Nuclei were stained blue with DAPI. Bar=20 µm.

DESCRIPTION OF SPECIFIC EMBODIMENTS OF THE INVENTION

The present invention, in some embodiments thereof, relates to induced pluripotent stem cells (iPS) derived from human pancreatic beta cells, uses thereof and methods of obtaining same.

The principles and operation of the cell populations according to the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1E:
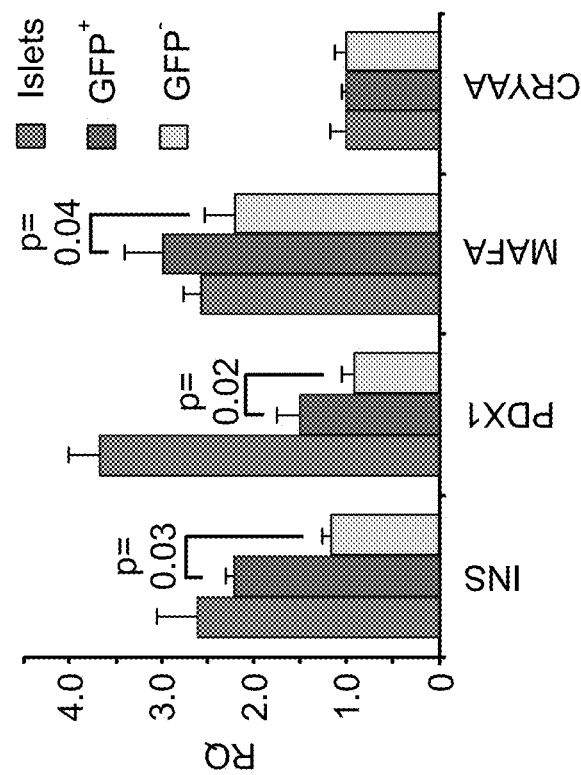
Figure 1D:
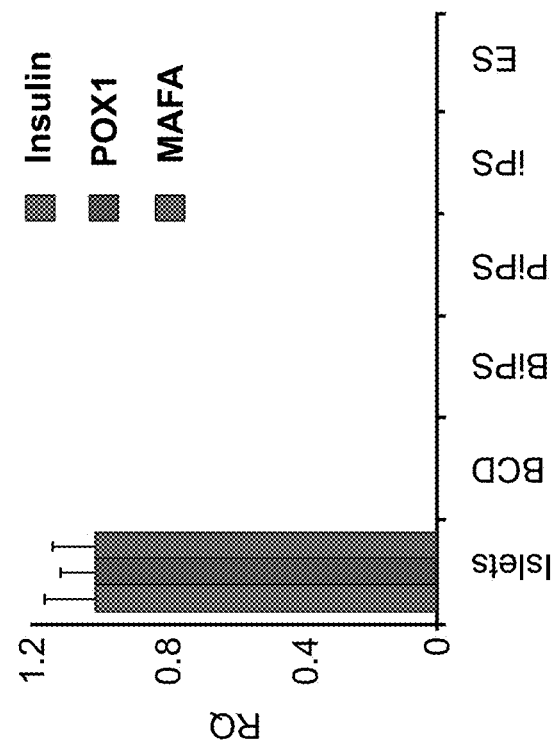
Figure 1F:
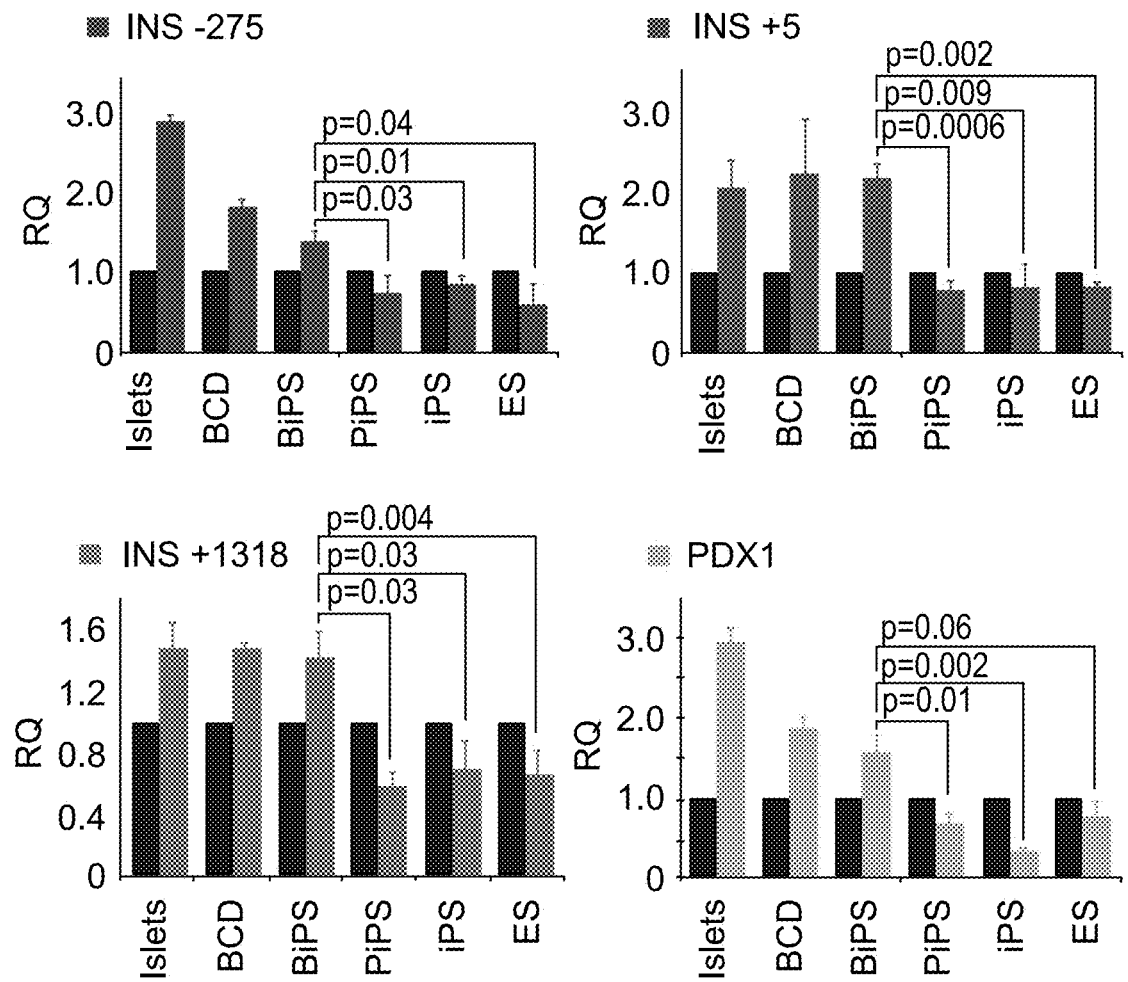
Figure 1I:
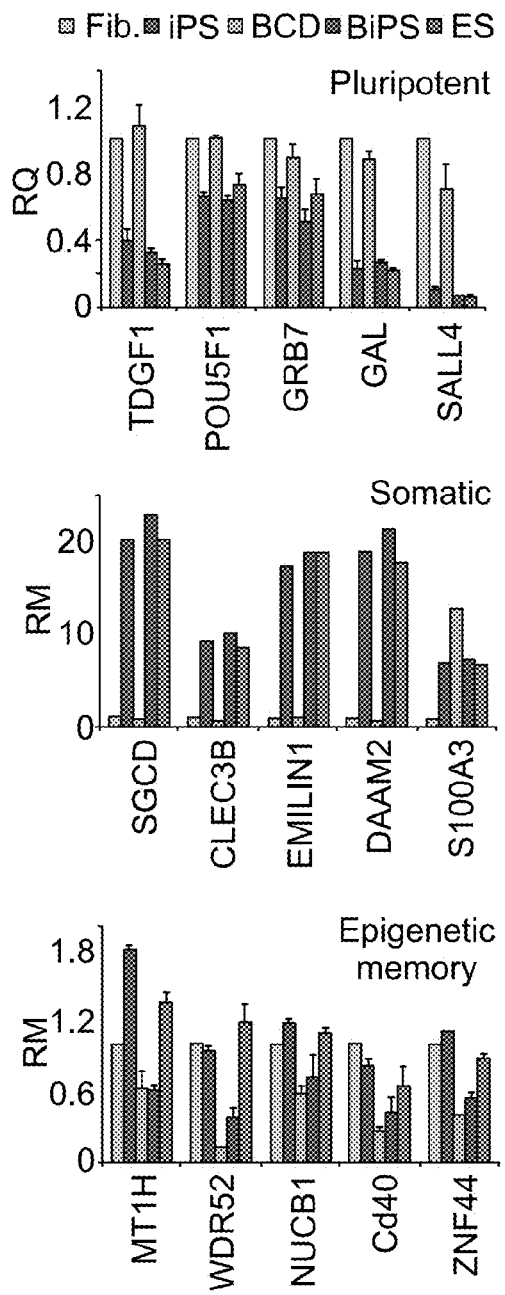
Figure 1J:
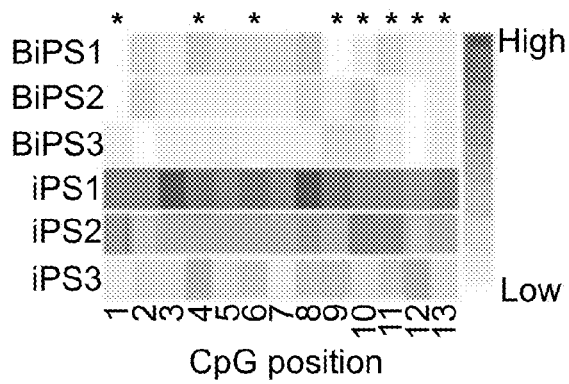
Figure 2A:
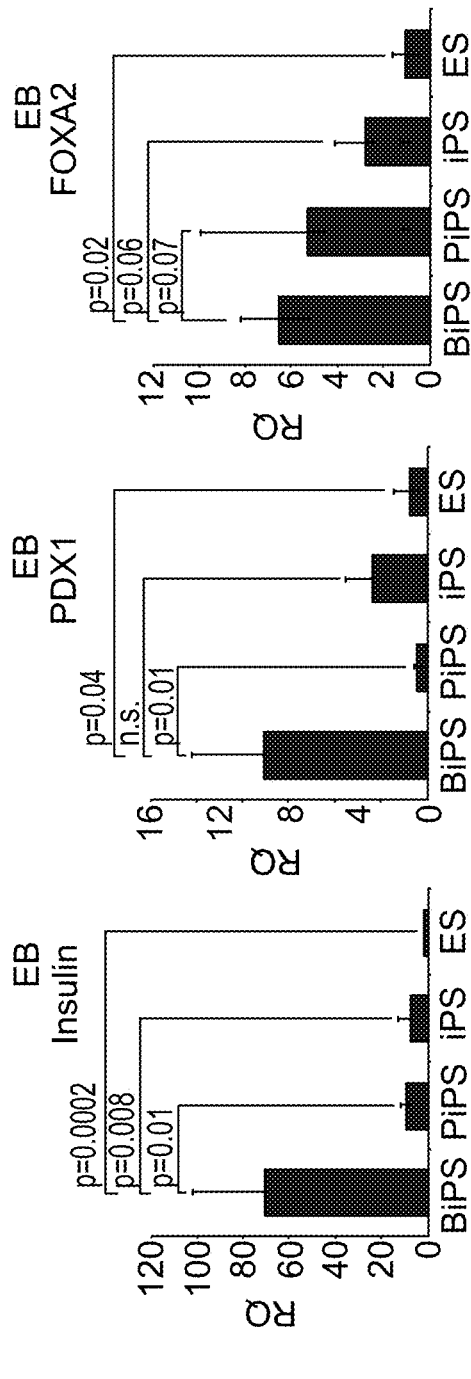
Figure 2B:
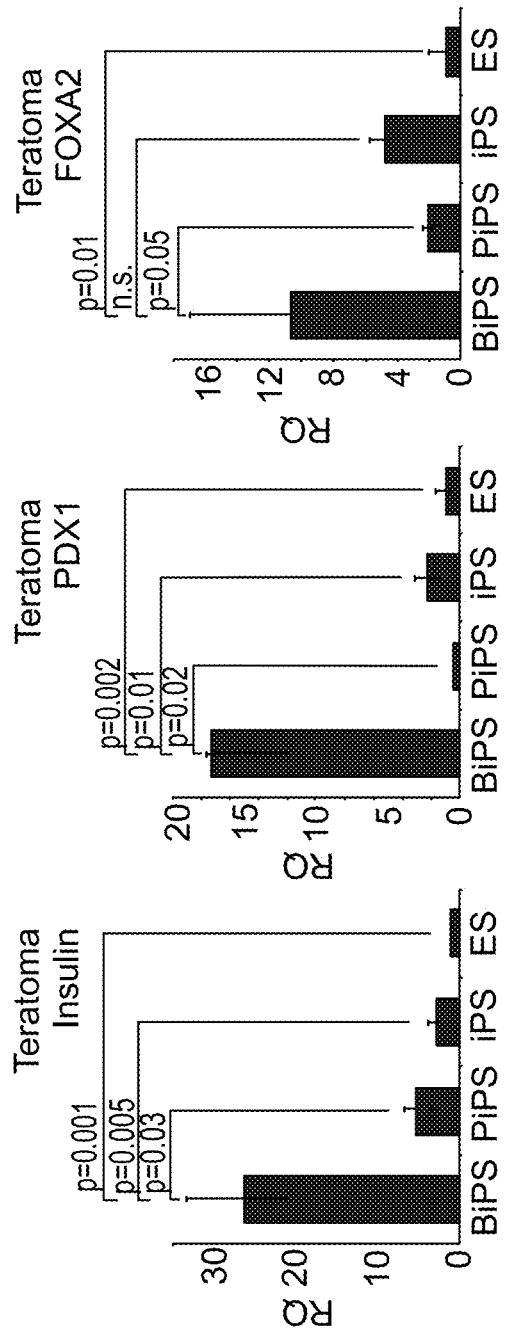
Figure 2D:
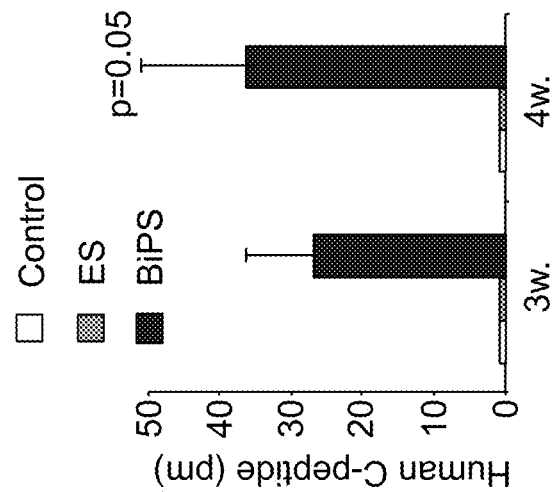
Figure 2C:
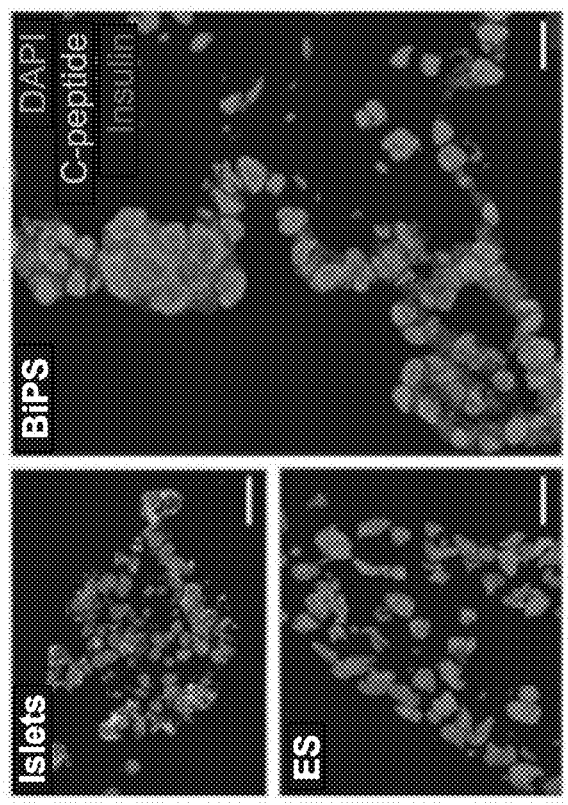
Figures 2E, 2F:
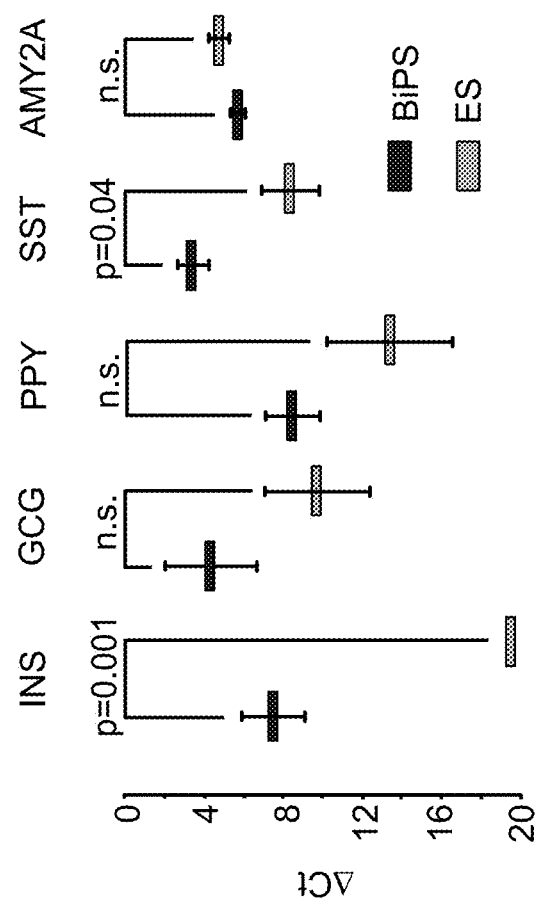
Figure 4C:
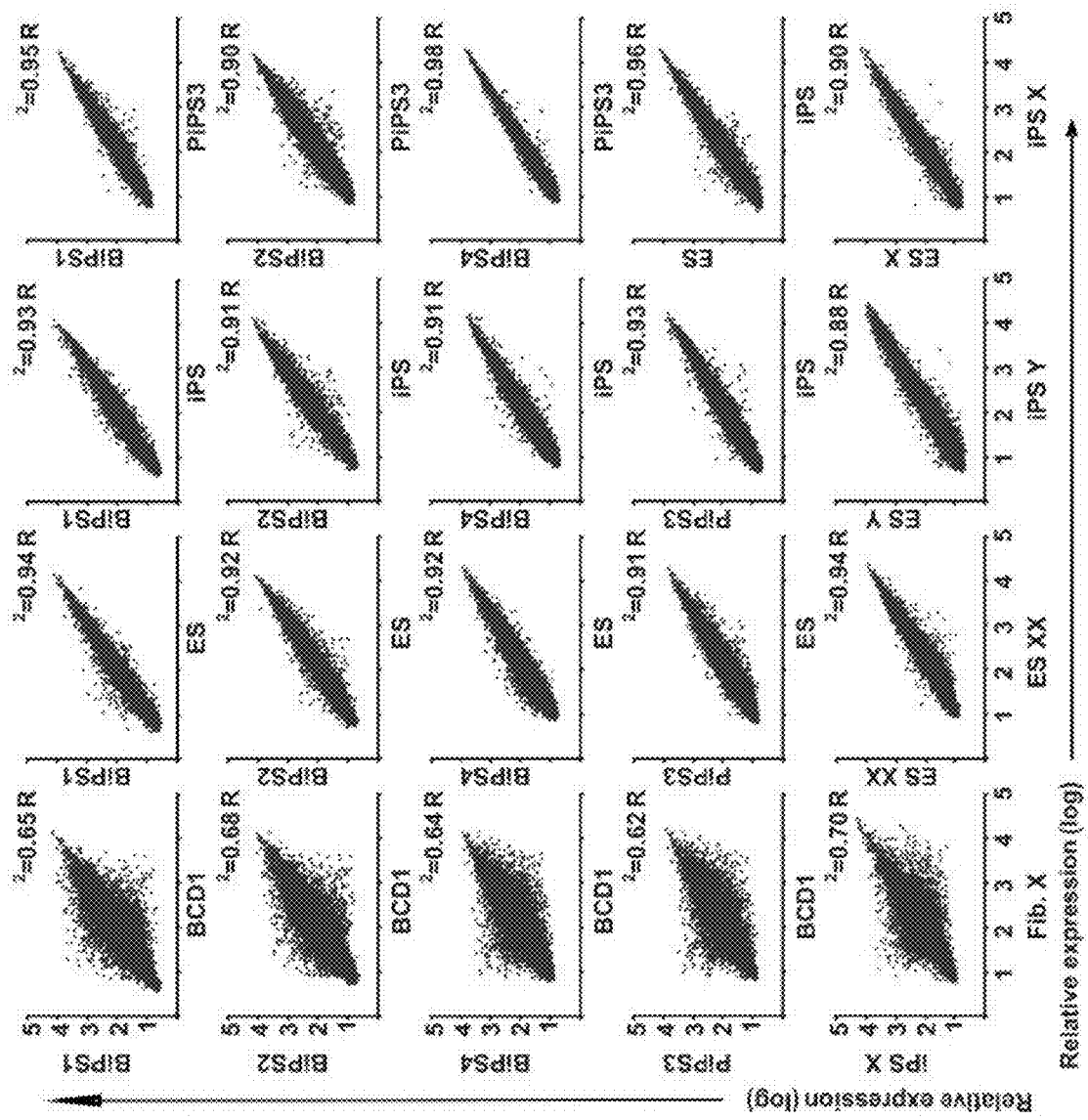
Figure 4E:
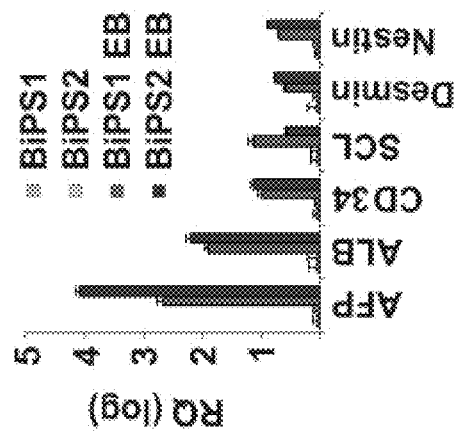
Figure 4D:
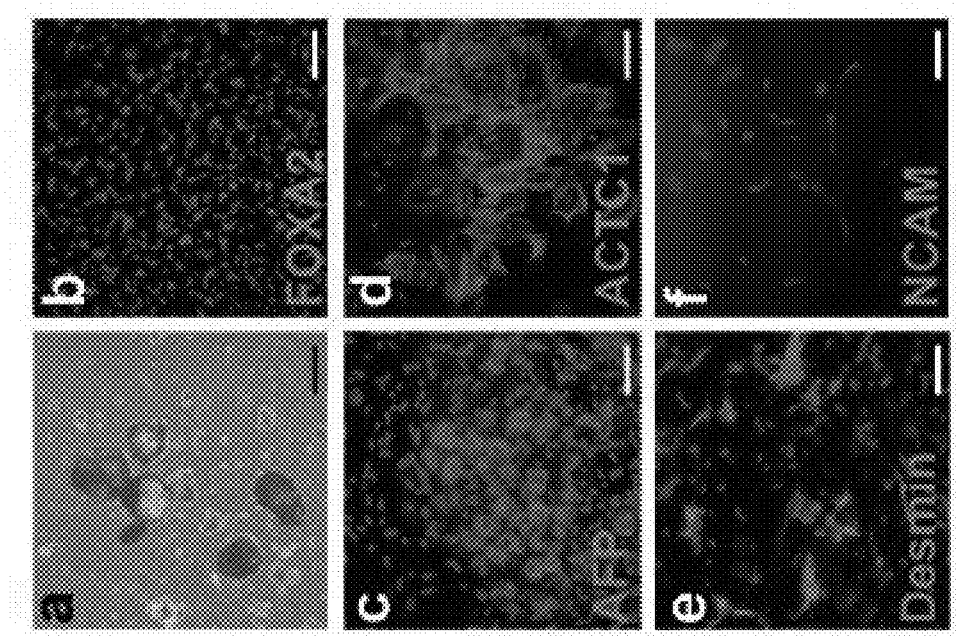

Human induced pluripotent stem (iPS) cells generated from somatic cells by expression of defined transcription factors are useful as a source of pluripotent cells which can be differentiated into a myriad of cell types for the treatment of diseases. The present inventors used two genetic lineage tracing systems in order to demonstrate generation of iPS cell lines from human pancreatic islet beta cells (FIGS. 1A-C). These reprogrammed cells acquired markers of undifferentiated pluripotent cells and can be differentiated into cells from the three embryonic germ layers (FIGS. 4D, E and F). However, the beta-cell-derived iPS (BiPS) cells maintained open chromatin structure at key beta-cell genes, together with a unique DNA methylation signature that distinguishes it from other pluripotent stem cells (FIGS. 1F-J). BiPS cells also demonstrated an increased ability to differentiate into insulin-producing cells in several differentiation assays in vitro and in vivo, compared with ES cells and isogenic non-beta iPS cells (FIGS. 2D-E). The present results suggest that the epigenetic memory may predispose BiPS cells to differentiate more readily into insulin producing cells. These findings demonstrate that human iPS cell phenotype may be influenced by their cell of origin, and suggest that their skewed differentiation potential may be advantageous for cell replacement therapy.

Thus, according to one aspect of the present invention there is provided a method of generating pluripotent stem cells, comprising:

(a) expanding human pancreatic beta cells; and subsequently (b) generating induced pluripotent stem (iPS) cells from the expanded human pancreatic beta cells.

As used herein, the term "pluripotent cell" refers to a cell that has the potential to divide in vitro for a long period of time (e.g., greater than one year) and has the unique ability to differentiate into cells derived from all three embryonic germ layers—endoderm, mesoderm and ectoderm. Pluripotent cells have the potential to differentiate into the full range of daughter cells having distinctly different morphological, cytological or functional phenotypes unique to different specific tissues. By contrast, descendants of pluripotent cells are progressively restricted in their differentiation potential, with some cells eventually having only one fate.

As used herein, the phrase "pancreatic beta cells" refers to pancreatic islet endocrine cells which are capable of secreting insulin in response to elevated glucose concentrations and express typical beta cell markers. Examples of beta cell markers include, but are not limited to, insulin, pdx, Hnf3β, PC1/3, Beta2, Nkx2.2, GLUT2 and PC2.

According to one embodiment the pancreatic beta cells are adult beta cells i.e. post-natal and non-embryonic.

The isolated pancreatic beta cells of this aspect of the present invention may be of homogeneous (i.e. purified pancreatic beta cells) or heterogeneous nature (i.e. a mixed cell population comprising, amongst the pancreatic beta cells, other additional pancreatic cells).

Thus, for example, the pancreatic beta cells of this aspect of the present invention may be comprised in isolated pancreatic islets. Islet cells are typically comprised of the following: 1) beta cells that produce insulin; 2) alpha cells that produce glucagon; 3) delta cells (or D cells) that produce somatostatin; and/or F cells that produce pancreatic polypeptide. The polypeptide hormones (insulin, glucagon, somatostatin and pancreatic polypeptide) inside these cells are stored in secretory vesicles in the form of secretory granules.

Methods of isolating islets are well known in the art. For example, islets may be isolated from pancreatic tissue using collagenase and ficoll gradients. An exemplary method is described in U.S. Pat. Appl. No. 20080014182, incorporated herein by reference.

According to another embodiment, the pancreatic beta cells of the present invention are dispersed into a single cell suspension—e.g. by the addition of trypsin or by trituration.

The pancreatic beta cells may be further isolated so that they are substantially free from other substances (e.g., other pancreatic cells, such as alpha cells and delta cells) that are present in its in-vivo environment e.g. by FACs sorting.

The pancreatic beta cells may be obtained from any autologous or non-autologous (i.e., allogeneic or xenogeneic) mammalian donor. For example, cells may be isolated from a human cadaver.

As used herein, the term "expanding" refers to increasing the number of pancreatic B cells by a process of cell division. It will be appreciated that during the expanding phase of the method of this aspect of the present invention the pancreatic beta cells undergo dedifferentiation. Preferably the expanding is effected for a number of passages such that the beta cells express a decreased amount of beta cell specific markers such as insulin or PDX-1, as assayed by Immunohistochemistry or RT-PCR.

It will be appreciated that the expanding is not effected for an amount of time which brings about cell senescence. Thus, the present invention contemplates expanding for about two weeks, about three weeks, about four weeks, about five weeks, about six weeks, about seven weeks, about eight weeks, about nine weeks, about 10 weeks, about 11 weeks, about 12 weeks, about 13 weeks, about 14 weeks, about 15 weeks or even about 16. According to a specific embodiment, the expanding is not effected for more than about 16 weeks. It will be appreciated that the specific amount of time will depend on the culturing conditions used and the culturing medium itself.

The present invention contemplates any medium for the expanding of the pancreatic beta cells.

According to one embodiment, the medium is CMRL-1066.

As used herein, the term "CMRL 1066" refers to the serum free medium, originally developed by Connaught Medical Research Laboratories for the culture of L cells, and includes any other derivations thereof provided that the basic function of CMRL is preserved. CMRL-1060 medium is commercially available in either liquid or powder form from companies including Gibco BRL, Grand Island, N.Y., catalogue number 11530-037; Cell and Molecular Technologies, Phillipsburg N.J.; Biofluids Inc, Rockville, Md.; Bioreclamation Inc. East Meadow, N.Y.; United States Biological, Swampscott, Mass.; Sigma Chemical Company, St. Louis, Mo.; Cellgro/Mediatech, Herndon, Va. and Life technologies, Rockville Md.

The medium used to culture the beta cells may further comprise supplementary constituents which may improve growth and/or viability thereof. These include, but are not limited to, growth factors (e.g. hepatocyte growth factor, nerve growth factor and/or epidermal growth factor) serum (e.g. fetal calf serum or fetal bovine serum), glucose (e.g. 5.6 mM) and antibiotics.

Non-apoptotic culturing conditions for pancreatic beta cells are known in the art—see for example U.S. Pat. Appl. No. 20080014182. According to one embodiment, beta cells are passaged every seven days and refed twice a week.

According to the teachings of U.S. Pat. Appl. No. 20080014182, pancreatic beta cells may be expanded 65,000 fold without any detectable apoptosis. According to another embodiment, the pancreatic beta cells are propagated as anchorage-dependent cells by attaching to a solid substrate (i.e., a monolayer type of cell growth).

According to still another embodiment, the expanding is effected in RPMI 1640 medium (e.g. containing 11 mM glucose, and supplemented with 10% FBS).

Following the expansion of the human pancreatic beta cells (and the concomitant generation of dedifferentiated cells therefrom), the present invention contemplates generating induced pluripotent stem cells therefrom.

According to one embodiment the method is effected by expressing in the cells at least one polypeptide belonging to the Oct family or the Sox family.

According to another embodiment, the method is effected by expressing in the cells at least two polypeptides—one belonging to the Oct family and one to the Sox family.

Examples of polypeptides belonging to the Oct family include, for example, Oct3/4 (NM_013633, mouse and NM_002701, human), Oct1A (NM_198934, mouse and NM_002697, human), Oct6 (NM_011141, mouse and NM_002699, human), and the like. Oct3/4 is a transcription factor belonging to the POU family, and is reported as a marker of undifferentiated cells (Okamoto et al., Cell 60:461-72, 1990). Oct3/4 is also reported to participate in the maintenance of pluripotency (Nichols et al., Cell 95:379-91, 1998).

Examples of polypeptides belonging to the Sox (SRY-box containing) family include, for example Sox1 (NM_009233, mouse and NM_005986, human), Sox3 (NM_009237, mouse and NM_005634, human), Sox7 (NM_011446, mouse and NM_031439, human), Sox15 (NM_009235, mouse and NM_006942, human), Sox17 (NM_011441, mouse and NM_022454, human) and Sox18 (NM_009236, mouse and NM_018419, human), and a preferred example includes Sox2 (NM_011443, mouse and NM_003106, human).

According to yet another embodiment, the method is effected by expressing in the cells four polypeptides—one belonging to the Oct family, one belonging to the Sox family, Nanog and lin28.

Alternatively, the method is effected by expressing in the cells four polypeptides—one belonging to the Oct family, one belonging to the Sox family, Klf-4 and c-Myc.

Expressing the dedifferentiating factors described herein above in the expanded pancreatic beta cells may be performed by genetic manipulation—example using expression constructs. Various methods can be used to introduce the expression vectors of the present invention into the pancreatic beta cells. Such methods are generally described in, for instance: Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass.; and Gilboa, E. et al. (1986). Transfer and expression of cloned genes using retroviral vectors. Biotechniques 4(6), 504-512; and include, for example, stable or transient transfection, lipofection, electroporation, and infection with recombinant viral vectors. In addition, see U.S. Pat. Nos. 5,464,764 and 5,487,992 for positive-negative selection methods.

Introduction of the expression constructs of the present invention into the pancreatic beta cells by viral infection offers several advantages over other methods such as lipofection and electroporation offering higher efficiency of transformation and propagation. According to a particular embodiment, expressing the dedifferentiating factors described herein above in the pancreatic beta cells is performed by retroviral transduction.

Methods of inducing iPS cells without viral integration are also contemplated—see for example Stadtfeld et al., 2008, [Science 322, 945-949] and Okita et al., 2008, [Science 322, 949-953].

Alternatively, the expanded pancreatic beta cells may be transfected with mRNAs encoding the dedifferentiating factors [Givol et al., BBRC 394 (2010): 189-193; Warren et al., Cell Stem Cell, Volume 7, Issue 5, 5 Nov. 2010, Pages 549-550] or by introduction of the proteins themselves (see for example Kim, D. et al. Cell Stem Cell doi:10.1016/j.stem.2009.05.005 (2009) and Zhou, H. Et al. Cell Stem Cell 4, 381-384, (2009).

As mentioned, the present inventors have found that iPS cells derived from a particular somatic cell type have a higher propensity to differentiate back into that cell type than an iPS cell derived from a different somatic cell type.

Accordingly, if a heterogeneous cell population is used as a starting material to generate the iPS cells (e.g. mixed population of pancreatic cells), the present inventors propose that a step of selection may be performed in order to ensure that the iPS cells obtained are derived from a particular somatic cell (e.g. pancreatic beta cell).

According to one embodiment, the selection is effected by permanently tagging the desired somatic cell (e.g. pancreatic beta cell) such that the tag remains even when the cell has been dedifferentiated into an iPS cell.

The phrase "permanently tagging" refers to incorporating a detectable moiety into, or on the surface of, the cells such that the detectable moiety remains in/on the cell irrespective of the differentiation status of the cell.

According to this aspect of the present invention, the tagging is effected prior to the expansion phase, whilst the B cell still expresses B cell markers (e.g. insulin). Typically, the tagging is effected no more than five days following culturing, and more preferably no more than three days following culturing.

Two exemplary methods for permanently tagging pancreatic beta cells are described in Example 1 herein below.

In brief, the mixed population including the pancreatic beta cells are transfected with two expression constructs. The first expression construct comprises a polynucleotide encoding a Cre recombinase polypeptide operatively linked to a pancreatic beta cell specific promoter. The Cre recombinase may be fused to an inducible promoter (e.g. estrogen receptor, which renders DNA recombination inducible by tamoxifen).

Examples of pancreatic B cell specific promoters include, but are not limited to an insulin promoter or a Pdx1 promoter.

The second expression construct comprises a first polynucleotide encoding a first detectable moiety operatively linked to a constitutive promoter, the first detectable moiety being flanked by LoxP polynucleotides. The second expression construct further comprises a second polynucleotide encoding a second detectable moiety, the second polynucleotide being positioned 3' to the first polynucleotide.

It will be appreciated that the tag (i.e. detectable moiety) may be any polypeptide which can be detected in a pancreatic beta cell throughout the course of its dedifferentiation, which itself does not influence pancreatic beta cell viability or dedifferentiation.

According to one embodiment, the tag is a light emitting protein.

Examples of tags which may be detected in pancreatic beta cells include, but are not limited to, light emitting protein genes such as green fluorescent proteins including EGFP (Enhanced Green Fluorescent Protein) and GFP (Green Fluorescent Protein), Red-2, cherry red, blue fluorescent protein (EBFP, EBFP2, Azurite, mKalamal), cyan fluorescent protein (ECFP, Cerulean, CyPet) and yellow fluorescent protein derivatives (YFP, Citrine, Venus, YPet) and LacZ gene.

Following generation of the iPS cells, iPS cells which are tagged may be isolated. Exemplary methods of isolating tagged cells include, but are not limited to manual dissection (microdissection) using a microscope capable of detecting the tag (e.g. fluorescent microscope) and sorting using a FACS sorter.

Purified populations of iPS cells derived from pancreatic beta cells may be used for a variety of purposes. According to one embodiment, they are used for screening candidate agents which affect proliferation and/or redifferentiation of dedifferentiated pancreatic B cells. Exemplary candidate agents include, but are not limited to small molecules, polypeptide agents and polynucleotide agents (e.g. siRNAs). According to another embodiment the purified populations of iPS cells derived from pancreatic beta cells are redifferentiated and used for cell therapy as further described herein below.

As mentioned, the present inventors have discovered that iPS cells derived from a particular somatic cell maintain open chromatin structure at genes specific to that somatic cell and display a unique DNA methylation signature.

Accordingly, the present inventors contemplate that the chromatin structure at genes specific to a particular somatic cell may be analyzed as well as the DNA methylation signature of the iPS cell in order to select for particular iPS cells.

Thus, for example in the case of an iPS cell derived from a pancreatic beta cell, the chromatin structure of the PDX-1 promoter or insulin promoter may be analyzed, wherein an open structure is indicative that the cell is derived from a pancreatic beta cell.

Methods of analyzing chromatin structure of particular genes are known in the art and include for example evaluating the levels of histone H3 acetylation, (a hallmark of open chromatin structure), by chromatin immunoprecipitation (ChIP).

DNA methylation levels may be analyzed using methods known in the art, e.g. using Illumina's Infinium HumanMethylation27 BeadChiP arrays and by pyrosequencing analysis. Exemplary genes that may be analyzed when the iPS cells are derived from pancreatic beta cells include, but are not limited to PDX-1, insulin, MT1H, WDR52, NUCB1, cd40 and ZNF4A.

As mentioned, the iPS cells of the present invention may be used in cell therapy for the treatment of diseases.

The present inventors have proved the existence of an epigenetic memory in cells derived from human beta cells during their expansion in vitro and have shown that this memory is maintained during reprogramming into iPS cells in most of the markers analyzed. Accordingly, the present inventors propose that iPS cells derived from a particular somatic cell have a higher propensity to express those somatic cell specific genes upon redifferentiation due to the relatively open chromatin structure of these loci.

Thus, the present invention contemplates that the source of the iPS cells for cell therapy is selected based on the particular somatic cell type that is required. Thus, for example, in the case of Diabetes, where insulin secreting cells are required, the present inventors propose that human beta cells be used as the source for iPS cells. In the case of neuronal diseases, the present inventors propose that human neuronal cells be used as the source for iPS cells. In the case of cardiac diseases, the present inventors propose that human cardiac cells be used as the source for iPS cells. In the case of liver diseases, the present inventors propose that human liver cells be used as the source for iPS cells etc.

Thus, according to another aspect of the present invention there is provided a method of generating cells useful for treating a disease associated with cellular malfunction, the method comprising:

(a) generating induced pluripotent stem cells from human somatic cells (either expanded, or not expanded), the human somatic cells being selected according to the cells which have mal-functioned in the disease; and (b) redifferentiating the induced pluripotent stem cells towards an original somatic lineage of the induced pluripotent stem cells, thereby generating cells useful for treating a disease associated with cellular malfunction.

According to one embodiment, healthy cells are used for the derivation of iPS cells.

According to another embodiment, the malfunctioning cells themselves are used for the derivation of iPS cells.

Methods of differentiating pluripotent stem cells into a particular cell type are known in the art and the present invention contemplates all such methods. The method may involve genetic modification of the cells and/or culturing of the cells in media comprising differentiating factors. It will be appreciated that the redifferentiating stage may result in the generation of fully differentiated cells or partially differentiated cells along a particular lineage.

According to a particular embodiment, iPS cells derived from pancreatic beta cells may be differentiated into pancreatic progenitor cells i.e. cells having a pancreatic lineage.

The phrase "pancreatic progenitor cells" refers to a population of cells which are not fully differentiated into pancreatic cells, yet are committed to differentiating towards at least one type of pancreatic cell—e.g. beta cells that produce insulin; alpha cells that produce glucagon; delta cells (or D cells) that produce somatostatin; and/or F cells that produce pancreatic polypeptide.

Typically, pancreatic progenitor cells express some of the phenotypic markers that are characteristic of pancreatic lineages (e.g. GLUT2, PDX-1 Hnf3β, PC1/3, Beta2, Nkx2.2 and PC2). Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent pancreatic progenitor cells may be present.

Typically, the iPS cells are initially differentiated into definitive endoderm cells. This may be carried out by culturing the iPS cells in a medium comprising activin A. Alternatively, the iPS cells may be cultured in a medium comprising small molecules known to induce definitive endoderm. Examples of such small molecules include, but are not limited to induced definitive endoderm 1 (IDE1) and induced definitive endoderm 1 (IDE2; see Borowiak et al., Cell Stem Cell 4, 348-358, 2009). The cells may then be cultured in additional differentiating factors including for example keratinocyte growth factor (KGF), retinoic acid and noggin in order to produce pancreatic progenitors. Other differentiating factors include, but are not limited to epidermal growth factor (EGF), nicotinamide, fibroblast growth factor (FGF), insulin like growth factor (IGF) and HGF.

Further examples of beta cell differentiation promoting agents include but are not limited to Activin A, Atrial Natriuretic Peptide, Betacellulin, Bone Morphogenic Protein (BMP-2), Bone Morphogenic Protein (BMP-4), C natriuretic peptide (CNP), Caerulein, Calcitonin Gene Related Peptide (CGRP-ax), Cholecystokinin (CCK8-amide), Cholecystokinin octapeptide (CCK8-sulfated), Cholera Toxin B Subunit, Corticosterone (Reichstein's substance H), Dexamethasone, DIF-1, Differanisole A, Dimethylsulfoxide (DMSO), EGF, Endothelin 1, Exendin 4, FGF acidic, FGF2, FGF7, FGFb, Gastrin I, Gastrin Releasing Peptide (GRP), Glucagon-Like Peptide 1 (GLP-1), Glucose, Growth Hormone, Hepatocyte Growth Factor (HGF), IGF-1, IGF-2, Insulin, KGF, Lactogen, Laminin, Leu-Enkephalin, Leukemia Inhibitory Factor (LIF), Met-Enkephalin, n Butyric Acid, Nerve Growth Factor (.beta.-NGF), Nicotinamide, n-n-dimethylformamide (DMF), Parathyroid Hormone Related Peptide (Pth II RP), PDGF AA+PDGF BB MIX, PIGF (Placental GF), Progesterone, Prolactin, Putrescine Dihydrochloride Gamma-Irradiated Cell Culture, REG1, Retinoic Acid, Selenium, Selenious Acid, Sonic Hedgehog, Soybean Trypsin Inhibitor, Substance P, Superoxide Dismutase (SOD), TGF-alpha, TGF-beta. sRII, TGF-beta.1, transferrin, Triiodothyronine (T3), Trolox, Vasoactive Intestinal Peptide (VIP), VEGF, Vitamin A and Vitamin E.

A beta cell differentiation promoting agent may also be a transcription factor. The term "beta cell differentiation transcription factor" as used herein is defined as any molecule, either a polypeptide or a nucleic acid expressing the polypeptide, which is involved in beta cell differentiation by functioning as a transcription factor. The transcription factor may also participate in additional mechanisms directed to development, metabolism or the like. Examples of beta cell differentiation transcription factor include, but are not limited to, NeuroD (GenBank Accession No. AAA93480), Pax6 (GenBank Accession No. AAK95849), Pax4 (GenBank Accession No. AAD02289), Nkx2.2 (GenBank Accession No. AAC83132), Nkx6.1 (GenBank Accession No. AAD11962), Is1-1 (GenBank Accession No. NP002193), Pd-x (GenBank Accession No. AAA88820) or Ngn3 (GenBank Accession No. AAK15022) and homologues or orthologues of same.

Polypeptide agents for promoting beta cell differentiation may be provided to the iPS cells or definitive endoderm cells differentiatied therefrom per se (i.e. added to the culture medium). Alternatively, polynucleotides encoding same may be administered to the iPS cells or definitive endoderm cells differentiatied therefrom. In this case, the polynucleotide agent is ligated in a nucleic acid construct under the control of a cis-acting regulatory element (e.g. promoter) capable of directing an expression of the beta cell differentiation promoting agent in the iPS cells or definitive endoderm cells differentiatied therefrom in a constitutive or inducible manner.

Below is a list of nine exemplary protocols for inducing differentiation of induced pluripotent stem cells into a pancreatic lineage. It will be appreciated that the list is non-limiting and all other differentiation protocols are contemplated by the present invention.

Protocol 1:

Protocol 1 is affected according to D-Amour et al [Nature Biotechnology, 2006] and Kroon et al [Nature Biotechnology, 2008] incorporated herein by reference.

Differentiation is carried out in RPMI supplemented with Glutamax and varying concentrations of FBS (0% for the first 24 hours, 0.2% for the second 24 hours and 2% for subsequent days of differentiation). The pluripotent stem cells are cultured with 100 ng/ml activin A and 25 ng/ml Wnt3a for the first 24 hours. The cells are then cultured in RPMI with 0.2% FBS and activin at 100 ng/ml for an additional 2 days. Next, the cells are cultured with RPMI with 2% FBS and KGF (25-50 ng/ml) for 3 days. The medium is changed to DMEM with 1% B27 supplement, KAAD-cyclopamine (0.25 µM) all-trans retinoic acid (2 µM) and Noggin (50 ng/ml) for 3 days. The medium is then changed to DMEM with 1% B27 for 3 days.

Protocol 2:

Protocol 2 is affected according to Jiang et al, [Stem Cell, 2007] incorporated herein by reference.

Stage 1—Confluent pluripotent stem cells are cultured in RPMI 1640 medium with 1× B27, 4 nM activin A and 1 mM Na-butyrate for 1 day. The medium is replaced with fresh RPMI 1640/B27 medium supplemented with 4 nM activin A and 0.5 mM Na-butyrate. The cells are cultured in this medium for another six days.

Stage 2—The cells are dissociated with collagenase IV and scraped off the plate in RPMI1640/B27 medium supplemented with 20 ng/ml EGF and 100 ng/ml Noggin and transferred to ultra low attachment plates. The cells are fed with fresh medium every 2-3 days for two weeks.

Stage 3—bFGF is withheld from the cultured after two weeks and cell clusters are cultured in suspension in RPMI 1640/B27 medium supplemented with EGF and Noggin for one week.

Stage 4—Cell clusters are cultured with fresh RPMI 1640 medium containing 0.5% BSA, 10 mM Nicotinamide and 50 ng/ml IGF II for 5 days and without IGF II for another 2 days.

Protocol 3:

Protocol 3 is affected according to Shim J H et al, [Diabetologia, 2007] incorporated herein by reference.

Pancreatic differentiation is initiated by treating hEBs sequentially with serum, activin and all-trans retinoic acid during EB formation. The hEBs are cultured in the presence of 20% fetal bovine serum for the first 4 days. The serum treated hEBs are then treated with 10-100 ng/ml activin A under serum free conditions for the following 6 days. Next, the hEBs were treated sequentially with retinoic acid 20% serum for 4 days, activin A 30 ng/ml for 4 days and retinoic acid (10 µmol/l) for 2 days. The hEBS are then dissociated and plated at a density of 100-150 clusters per 35 mm tissue culture dish in insulin-transferrin-selenite (ITS) medium containing fibronectin (5 µg/ml).

Protocol 4:

Protocol 4 is affected according to Frandsen et al, [BBRC, 2007] incorporated herein by reference.

Human pluripotent stem cells are differentiated as embryoid bodies. Activin B (50 ng/ml) is added to the embryoid bodies for two weeks.

Protocol 5:

Protocol 5 is affected according to Tateishi et al, [JBC, 2008] incorporated herein by reference.

Differentiation of pluripotent stem cells is initiated in RPMI 1640 supplemented with B27 and 4 nM activin A for 7 days. Sodium butyrate is added on day 1 at a final concentration of 0.1 mM (stage 1). After stage 1, the cells are dissociated with collagenase IV and transferred into ultra low attachment plates. The cell aggregates are cultured in RPMI 1640 supplemented with B27, 20 ng/ml epidermal growth factor, 2 ng/ml basic fibroblast growth factor and 100 ng/ml noggin for 2 weeks (stage 2). At stage 3, cell clusters are cultured in suspension in RPMI 1640 supplemented with B27, 20 ng/ml epidermal growth factor and 100 ng/ml Noggin for 1 week. Finally, the cells are incubated in RPMI 1640 medium with 0.5% bovine serum albumin, 10 mM nicotinamide and 50 ng/ml insulin like growth factor II for another 2 days (stage 4).

Protocol 6:

Protocol 6 is affected according to Gao et al, [Translational Research, 2008] incorporated herein by reference.

Protocol 7:

Protocol 7 is affected according to Chen et al, [Nature Chemical Biology, 2009] incorporated herein by reference.

To generate a definitive endoderm population, pluripotent stem cells are cultured on MEF feeder cells until 80-90% confluent, then treated with 25 ng/ml Wnt3a (R&D), 100 ng/ml activin A (R&D) in advanced RPMI (Invitrogene) supplemented with 1XL-glutamine for 1 d then 100 ng/ml activin A in advanced RPMI supplemented with 1XL-glutamine and 0.2% (v/v) fetal bovine serum (FBS, BetHaemek). The medium is changed 2 d later to 50 ng/ml FGF10 (R&D), 0.25 mM KAAD-cyclopamine (Sigma) in advanced RPMI supplemented with 1XL-glutamine and 2% FBS and maintained for an additional 2 d. Cells are then transferred to 50 ng/ml FGF10, 0.25 µM KAAD cyclopamine, 2 µM retinoic acid (Sigma) in DMEM supplemented with 1XL-glutamine and 1XB27 (Invitrogen) and cultured for an additional 4 d with or without 300 nM ILV (Axxora). For additional differentiation the cells are cultured for 6 d in DMEM supplemented with 1XL-glutamine, 1% B27, 50 ng/ml exendin (Sigma) and 10 µM DAPT (Sigma). At the final stage the cells are cultured for 6 d in CMRL (Invitrogen) supplemented with 1XL-glutamine, 1% B27, 50 ng/ml HGF (Bet-Haemek) and 50 ng/ml IGF (Bet-Haemek).

Protocol 8:

Protocol 8 is affected according to Borowiak et al, [Cell stem cells 2009] incorporated herein by reference.

Protocol 9:

Protocol 9 is affected according to Johannesson M et al, [PLOS 2009] incorporated herein by reference.

For differentiation, the cells are grown until confluence. The medium is changed to activin A 100 ng/ml and Wnt3A 25 ng/ml in RPMI 1640 supplemented with no FBS for the first day and 0.2% FBS the second and third day. On days four to seven RPMI 1640 is supplemented with 2% FBS and from day eight DMEM is supplemented with 2% FBS. From day four onward, FGF4 (1.1 ng/ml) and retinoic acid (2 µM) were added.

The present invention further contemplates isolated cell populations generated according to the methods described herein.

It will be appreciated that the term "isolated" as used herein refers to a cell population outside the body and does not necessarily refer to a purified homogeneous cell population.

As mentioned, the redifferentiated cells of this aspect of the present invention may be transplanted into patients in order to treat diseases. Thus, for example, iPS cells derived from pancreatic beta cells and redifferentiated towards a pancreatic lineage may be used to treat Diabetes.

As used herein "Diabetes" refers to a disease resulting either from an absolute deficiency of insulin (Type 1 Diabetes) due to a defect in the biosynthesis or production of insulin, or a relative deficiency of insulin in the presence of insulin resistance (type 2 Diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the redifferentiated pancreatic beta cells of the present invention, using any suitable route. Typically, beta cell therapy is effected by injection using a catheter into the portal vein of the liver, although other methods of administration are envisaged.

As mentioned hereinabove, the pancreatic beta cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycin-namylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The redifferentiated pancreatic beta cells of the present invention may be transplanted to a subject per se, or in a pharmaceutical composition where they are mixed with suitable carriers or excipients. Similarly, the agent of the present invention may be administered to a subject per se, or in a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the redifferentiated pancreatic cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Typically, the pharmaceutical composition is administered in a local rather than systemic manner, for example, via injection of the pharmaceutical composition directly into a tissue region of a patient.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations of C peptide and/or insulin.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser advice may be a syringe. The syringe may be prepacked with the cells. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is expected that during the life of a patent maturing from this application many relevant methods for generating iPS cells will be developed and the present application is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, N.Y.; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed.

(1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND METHODS

Cell Culture:

Human islets were received 1-3 days following isolation. Islet purity was 79±9%, as determined by staining with dithizone. Islets from individual donors (age average 49±18 years) were dissociated into single cells, and beta cells were labeled and cultured as previously described [Russ, H. A., et al., Diabetes 57, 1575-1583 (2008): Russ, H. A., et al., PLoS One 4, e6417 (2009)] in CMRL 1066 (Biological Industries, Beit Haemek, Israel) supplemented with 10% FCS (Biological Industries, Beit Haemek, Israel), penicillin (50 units/ml) and streptomycin (50 µg/ml) (Gibco-Invitrogen). ES cells (H9, HUES13 and CSES2 cell lines), iPS cell lines [Pick, M. et al. Stem Cells 11, 2686-2690 (2009); Urbach, A., et al., Cell Stem Cell 6, 407-411 (2010)], PiPS and BiPS cells were maintained on mouse embryonic fibroblast (MEF) feeder layer and cultured in standard ES cell culture medium containing KnockOut DMEM (Gibco-Invitrogen) supplemented with 15% KnockOut serum replacement (Gibco-Invitrogen), 2 mM L-glutamine (Sigma-Aldrich), 1:100 dilution of non-essential amino acids (Gibco-Invitrogen), 0.1 mM β-mercaptoethanol (Sigma-Aldrich), 8 ng/ml basic fibroblast growth factor (bFGF, PeproTech), penicillin (50 units/ml) and streptomycin (50 µg/ml) (Gibco-Invitrogen). Cells were passaged enzymatically using 0.25% trypsin (Biological Industries, Beit Haemek, Israel). Foreskin fibroblasts were grown in DMEM supplemented with 10% FCS (Biological Industries, Beit Haemek, Israel), penicillin (50 units/ml) and streptomycin (50 µg/ml) (Gibco-Invitrogen).

Cell Sorting:

Labeled cells were sorted using a FACS Aria cell sorter (Becton Dickinson, San Jose, Calif.) as described (1,2).

Viral Vector Production:

For beta-cell labeling, DeltaU3 virus particles for both lineage tracing systems were produced as previously described [Russ, H. A., et al., Diabetes 57, 1575-1583 (2008): Russ, H. A., et al., PLoS One 4, e6417 (2009)]. Briefly, the lentiviral vectors pTrip RIP405 nlsCRE DeltaU3, pTrip CMV-loxP-DsRed2-loxP-eGFP DeltaU3, pTrip RIP405 CRE-ERT2 DeltaU3 and pTrip-loxP-NEO-STOP-loxP-eGFP were each co-transfected with the pCMVdR8.91 and pMD2.G plasmids in 293T cells, and culture medium was harvested every 24 hours for 3 days.

iPS Cell Generation:

Approximately $2 \times 10^6$ 293T cells were transfected in the presence of TransIT™-LT1 (Mirus) with 4.5 µg of pMXs retroviral vectors containing either human OCT4, SOX2, KLF4 or cMYC genes (Addgene) and 4.5 µg of PCL-Amphotropic plasmid. Twenty four hours after transfection the culture medium was replaced with fresh medium, and 48 hours after transfection the supernatant was collected, filtered through a 0.45-µM cellulose acetate filter (Whatman) and supplemented with 8 µg/ml Polybrene (Sigma-Aldrich). Virus-containing medium was then transferred to a 10-cm dish containing $2\text{-}10 \times 10^6$ islet cells (between passages 3-9). Seventy two hours later, a second round of infection was performed. Four days post infection ES cell medium was added to the infected islet cells, and mitomycin-treated MEFs were seeded onto the dish. Between 30-40 days post infection, ES-like colonies were picked and allowed to propagate in a 12-well plate. At this stage the culture was defined as passage 0 and passaged mechanically until passage 2. Thereafter cultures were passaged using 0.25% trypsin. Generation of foreskin fibroblast iPS cells was performed as previously described [Pick, M. et al. Stem Cells 11, 2686-2690 (2009); Urbach, A., et al., Cell Stem Cell 6, 407-411 (2010)].

Karyotype Analysis:

Cells in log growth phase in a 10-cm plate were treated with colcemid (Biological Industries, Beit Haemek, Israel) at a final concentration of 100 ng/ml, then harvested with trypsin, treated with hypotonic solution and fixed. Metaphases were spread onto glass slides and stained with giemsa dyes (Sigma-Aldrich). Chromosomes were classified according to the International System for Human Cytogenetic Nomenclature. At least 20 metaphases were analyzed per each cell line.

DNA PCR Analysis:

Total genomic DNA was extracted using genomic DNA extraction kit (RBC). PCR analysis of the integrated reporter vector of lineage-tracing system 1 was performed as described [Russ, H. A., Diabetes 57, 1575-1583 (2008)]. Primers to detect the integrated RIP-CRE/ER fragment were: sense primer 5'GAGACAATGTCCCCTGCTGT3' (SEQ ID NO:1) and anti sense primer 5'CCTGGACTTTGCTGTTTGT3' (SEQ ID NO:2) amplifying a 210 bp product. For PCR analysis of the integrated reporter vector of lineage-tracing system 2, the sense primer 5'ATCCACGCTGTTTTGACCTG3' (SEQ ID NO:3) and the antisense primer 5'AAGTCGTGCTGCTTCATGTG3' (SEQ ID NO:4) were used. This primer pair amplifies a 1399-bp fragment from the original sequence and a 439-bp fragment from the recombined sequence. PCR products were resolved on a 1.5% agarose gel containing ethidium bromide.

DNA Methylation Arrays:

The HumanMethylation27 BeadChip comprises 27,578 array probes CpG sites representing 14,495 genes with an average of two probes per gene. Following bisulfite conversion of 500 ng of genomic DNA (EZ-DNA Methylation Kit, Zymo Research Corporation, CA, worldwidewebdot zymoresearchdotcom), samples were whole genome amplified, enzymatically fragmented, and 200 ng DNA was applied to BeadChips (Illumina, CA, wwwdotilluminadotcom). DNA methylation levels were scored as β values using Illumina's Genome studio software. Hierarchical clustering was performed using Partek software.

Pyrosequencing Analysis:

Pyrosequencing was performed by EpigenDx (Worcester, Mass.) using the PSQ™96HS system according to standard procedures with a unique set of primers that were developed by EpigenDx for the CpG sites of the PDX1 promoter (Human PDX1 ADS1159) at positions (−1087) to (−849) from the cap site of the PDX1 gene.

Chromatin Immunoprecipitation (ChIP):

Approximately $1.5 \times 10^6$ cells were crosslinked with formaldehyde solution, lysed and their chromatin was sonicated to 200-1000-bp fragments. The chromatin was then pre-cleared using 30 µL of salmon sperm agarose beads (Upstate Biotechnology) for 1 hour at 4° C. Immunoprecipitation was performed overnight using anti-acetylated histone H3 antibody (Upstate Biotechnology). The crosslinking was reversed, and DNA was recovered using a PCR clean-up kit (Qiagen). Eluted DNA fragments were used for quantitative PCR analysis with primers listed in Table 1. All reactions were performed in triplicate with annealing at 60° C. for 40 cycles.

TABLE 1

Primer sets for DNA qPCR

| Antisense primer | Sense primer | Locus |
| --- | --- | --- |
| TCCTCAGGACCAGCGGG (SEQ ID NO: 6) | TGTGAGCAGGGACAGGTCTG (SEQ ID NO: 5) | INS -275 |
| GTCCAGCCACCCTGGAATC (SEQ ID NO: 8) | TCAGAAGAGGCCATCAAGCA (SEQ ID NO: 7) | INS +5 |
| GCTGGTTCAAGGGCTTTATTCC (SEQ ID NO: 10) | CAGCTGGAGAACTACTGCAACTAGA (SEQ ID NO: 9) | INS +1318 |
| CGGAACGTAGCTTCCCAATA (SEQ ID NO: 12) | AGAGTCGTCAAGGGTCTGGA (SEQ ID NO: 11) | PDX1 promoter |
| CTTATCCCCATGGCAACTCA (SEQ ID NO: 14) | CCTCTTCCCACAGCTGTTTC (SEQ ID NO: 13) | MAFA promoter |
| AGCCGGCTGGGGTAGAAG (SEQ ID NO: 16) | CCGTGGTACCAAAGCTGA (SEQ ID NO: 15) | Crystallin |

RNA qRT-PCR Analyses:

Total RNA was extracted using RNAeasy™ Mini Kit (Qiagen) according to the manufacturer's instructions. One microgram of total RNA (DNase-treated) was reverse-transcribed with random hexamer primers using ImProm-II reverse transcriptase (Promega). For differentiation analyses of teratomas and directed differentiation, total RNA was isolated using Trizol (Sigma-Aldrich) and treated with DNA-free (Ambion) to remove genomic DNA. cDNA was prepared using High Capacity cDNA RT Kit (Applied Biosystems). qRT-PCR was carried out in triplicates using Power SYBR Green or TaqMan Universal PCR Master Mix (Applied Biosystems) in 7300 Real-time PCR System (Applied Biosystems). The results were normalized to glyceraldehyde-3-phosphate dehydrogenase (GAPDH) and/or ubiquitin C (UBC) transcripts. Table 2 lists primer sequences. All reactions were performed with annealing at 60° C. for 40 cycles. For undetectable transcripts, the cycle number was set to 40 for comparisons.

TABLE 2

Primer sets for RNA qRT-PCR

| Antisense primer | Sense primer | Gene |
| --- | --- | --- |
| Taqman probe Hs_03005111_g1 | Taqman probe Hs_03005111_g1 | OCT3/4 |
| Taqman probe Hs_00702808_s1 | Taqman probe Hs_00702808_s1 | LIN28 |
| Taqman probe Hs00173564_m1 | Taqman probe Hs00173564_m1 | FGF4 |
| TTGCGTGAGTGTGGATGGGATTGGTG (SEQ ID NO: 18) | GGGAAATGGGAGGGGTGCAAAAGAGG (SEQ ID NO: 17) | SOX2 |
| CCTGAATAAGCAGATCCATGG (SEQ ID NO: 20) | CATGAGTGTGGATCCAGCTTG (SEQ ID NO: 19) | NANOG |
| TCTTGTCTTTGCCCGTTTCT (SEQ ID NO: 22) | TCACAGTCCAGCAGGTGTTTG (SEQ ID NO: 21) | REX1 |
| Taqman probe Hs_00824723_m1 | Taqman probe Hs_00824723_m1 | UBC |
| GTACTCAGCGGCCAGCATCG (SEQ ID NO: 24) | AGCCACATCGCTCAGACACC (SEQ ID NO: 23) | GAPDH |
| CCCTTTTTCTGGAGACTAAATAAA (SEQ ID NO: 26) | CCCCAGGGCCCCATTTTGGTACC (SEQ ID NO: 25) | OCT3/4 (Tg) |
| TTATCGTCGACCACTGTGCTGCTG (SEQ ID NO: 28) | GGCACCCCTGGCATGGCTCTTGGCTC (SEQ ID NO: 27) | SOX2 (Tg) |
| CCCTTTTTCTGGAGACTAAATAAA (SEQ ID NO: 30) | ACGATCGTGGCCCCGGAAAAGGACC (SEQ ID NO: 29) | KLF4 (Tg) |

TABLE 2-continued

Primer sets for RNA qRT-PCR

| Antisense primer | Sense primer | Gene |
|---|---|---|
| CCCTTTTTCTGGAGACTAAATAAA (SEQ ID NO: 32) | CAACAACCGAAAA TGCACCAGCCCCAG (SEQ ID NO: 31) | cMyc (Tg) |
| Taqman probe Hs 00355773 m1 | Taqman probe Hs 00355773 m1 | INS |
| Taqman probe Hs_00426216_m1 | Taqman probe Hs_00426216_m1 | PDX1 |
| Taqman probe Hs_00232764_m1 | Taqman probe Hs_00232764_m1 | FOXA2 |
| Taqman probe Hs_00173490_m1 | Taqman probe Hs_00173490_m1 | AFP |
| Taqman probe Hs_00609403_m1 | Taqman probe Hs_00609403_m1 | ALB |
| Taqman probe Hs_00268434_m1 | Taqman probe Hs_00268434_m1 | SCL |
| Taqman probe Hs_00156373_m1 | Taqman probe Hs_00156373_m1 | CD34 |
| Taqman probe Hs_00157258_m1 | Taqman probe Hs_00157258_m1 | DES |
| Taqman probe Hs_99999905_m1 | Taqman probe Hs_99999905_m1 | GAPDH (h) |
| Taqman probe Hs_00707120_s1 | Taqman probe Hs_00707120_s1 | NESTIN |
| Taqman probe Hs_00158126_m1 | Taqman probe Hs_00158126_m1 | ISL1 |
| Taqman probe Hs01651425_s1 | Taqman probe Hs01651425_s1 | MAFA |
| Taqman probe Hs00165941_m1 | Taqman probe Hs00165941_m1 | TH |
| Taqman probe Hs01031536_m1 | Taqman probe Hs01031536_m1 | GCG |
| Taqman probe Hs00174949_m1 | Taqman probe Hs00174949_m1 | SST |
| Taqman probe Hs00237001_m1 | Taqman probe Hs00237001_m1 | PPY |
| Taqman probe Hs00420710_g1 | Taqman probe Hs00420710_g1 | AMY2A |
| Taqman probe Hs00232355_m1 | Taqman probe Hs00232355_m1 | NKX6-1 |

Alkaline Phosphatase Staining:

Alkaline phosphatase staining was performed using the Leukocyte Alkaline Phosphatase Kit (Sigma-Aldrich) according to the manufacturer's instructions.

Immunofluorescence Analyses:

For immunostaining of pluripotency-related genes and markers of differentiation of plated EBs, cells were washed twice with PBS, crosslinked with 10% formalin solution (Bi-olabs) for 10 min, washed twice with PBS and blocked for 1 hr. at room temperature with PBS containing 2% bovine serum albumin (BSA, Sigma-Aldrich) and 0.1% Triton-X-100 (Sigma-Aldrich). Primary antibodies diluted in blocking solution were added for 1 hour at room temperature. Cells were washed and incubated for 40 min with the appropriate secondary Cy3 antibody (1:200, Jackson Immunoresearch laboratories). The primary antibodies used were: mouse anti-human OCT3/4 (IgG, 1:200, Santa Cruz Biotechnology), goat anti-human SOX2 (IgG, 1:100, Santa Cruz Biotechnology), goat anti-human NANOG (IgG, 1:100, R&D Systems), mouse anti-human Tra-1-60 (IgM, 1:500, Santa Cruz Biotechnology), rabbit anti-human alpha-fetoprotein (IgG, 1:200, Dako), rabbit anti-human FOXA2 (IgG, 1:1000, Abcam), mouse anti-human Desmin (IgG, 1:200, Dako), mouse anti-human cardiac fetal actin (IgG, 1:200, Maine Biotechnology), and goat anti-human NCAM1 (IgG, 1:150, R&D Systems). For immunostaining of sectioned EBs (20 days) and human islets, EBs or islets were fixed in 4% paraformaldehyde (PFA) on ice for 1 hr. and 2 hrs., respectively. Following washing in PBS, EBs and islets were embedded in Tissue Tek and snap-frozen over liquid nitrogen. Ten-μm sections were cut using a CM3050S cryostat (Leica). Sections were post-fixed for 10 minutes in 4% PFA at room temperature, followed by washing in PBS. Sections were blocked and permeabilized for 20 min with 5% fetal goat serum, 1% BSA, and 0.2% saponin, and incubated overnight at 4 C.° with the primary antibodies diluted in blocking solution. Primary antibodies were mouse anti-human C-peptide (1:100, Biodesign), goat anti-human PDX1 (1:500, RnD systems), and guinea-pig anti-insulin (1:500, Dako). Slides were then washed and incubated for 40 min with the appropriate ALEXA-conjugated secondary antibodies (Invitrogen). DNA was stained with DAPI (Sigma-Aldrich, St. Louis, Mo.). Images were taken using a Leica SP-5 confocal, Zeiss LTM 200 ApoTome, or OlympusIX70 microscopes. Images of fluorescent living cells were taken with a long-distance objective on OlympusIX70 microscope.

DNA Microarray Analysis:

Total RNA (DNase-treated) was extracted using RNAeasy Mini Kit (Qiagen) according to the manufacturer's instructions kit (Affymetrix, Santa Clara, Calif.) according to the manufacturer's protocol. Hybridization to the GeneChip Human Gene 1.0 ST Arrays (Affymetrix), washing and scanning were performed according to the manufacturer's protocol. Expression patterns were compared between samples and hierarchical clustering expression was performed using Expander (EXPression Analyzer and DisplayER) software.

In-Vitro Differentiation of ES and iPS Cells:

To initiate embryoid body (EB) formation, a semi-confluent 10-cm plate of ES or iPS cells was harvested using trypsin, and cell clumps were resuspended in ES cell medium without bFGF, allowed to aggregate and transferred to one well of a non-adherent 6-well plate. After 8 days as floating EBs, cell clumps were collected and seeded in a 12-well adherent culture dish. After an additional 8 days of growth, adherent cells were stained for markers of the three embryonic germ layers. Alternatively, EBs were allowed to undergo spontaneous differentiation for 20 days in suspension, after which they were collected and taken for RNA and protein analyses.

In-Vivo Differentiation of ES and iPS Cells:

A confluent 10-cm plate was harvested using trypsin. Cells were centrifuged, and cell pellets were resuspended in 50 μL of iPS cell medium. The iPS or ES cells were injected under the renal capsule of SCID-Beige male mice (2-6-month-old) (Harlan, Jerusalem, Israel) as described [Russ et al., Methods in Bioengineering, Yarmush M L, Langer R S (eds.), Artech House, in press]. Tumors were dissected after 4 weeks following injection. A portion of the graft was used for RNA isolation and another part was processed for paraffin embedding. Sections were stained with haematoxylin and eosin. Images were acquired using a Zeiss LTM 200 Apotome.

Induced Differentiation of ES and iPS Cells:

Differentiation of ES and iPS cells into pancreas endocrine progenitor cells was induced according to the Novocell protocol [Kroon et al., Nat. Biotechnol. 26, 443-452 (2008)] with the following modifications: 80-90% confluent ES and iPS cell cultures were washed twice with PBS and incubated in RPMI (Sigma-Aldrich) containing Activin A (PeproTech, 100 ng/ml) for 1 day. Subsequently, the medium was changed daily for the duration of the protocol. In the next 2 days, cells were cultured in RPMI containing 0.02% FBS (vol/vol) and Activin A (100 ng/ml). On day 4, the medium was changed to RPMI with 2% FBS (vol/vol) and KGF (PeproTech, 25 ng/ml) for 3 days. Next, cells were incubated for 3 days in RPMI with 2% FBS (vol/vol), KAAD-cyclopamine (Calbiochem, 0.25 μM), all-trans retinoic acid (Sigma-Aldrich, 2 μM), and Noggin (PeproTech, 50 ng/ml). The medium was changed for the following 3 days to DMEM containing 1% B27 (Gibco-Invitrogen, vol/vol). Differentiated cells from a confluent 10-cm plate were harvested, and an aliquot was taken for RNA analysis. $2.5$-$4 \times 10^6$ cells were injected under the renal capsule of SCID male mice as indicated above. Starting 21 days post-transplantation, graft maturation was assessed by measuring serum human C-peptide levels. Mice were fasted for 20 hours and injected intraperitoneally with 3 g D-glucose in PBS per kg body weight. Serum samples were collected 30 min following glucose administration as described [Russ et al., Methods in Bioengineering, Yarmush M L, Langer R S (eds.), Artech House (in press).]. Human C-peptide levels were quantified using an ultrasensitive ELISA kit (Mercodia) according to the manufacturer's instructions (the assay sensitivity is set to 1.5 pmol/L). The assay cross-reactivity with insulin and proinsulin is <0.0006% and <1.8%, respectively. Mice were sacrificed at the indicated time points, and the graft-containing kidneys were removed and analyzed as detailed above for teratomas.

Statistical Analysis:

Significance was determined using one- or two-tailed t-test. To approach a normal distribution of the qRT-PCR data, a logarithmic transformation was performed.

Example 1

Confirmation of the Pancreatic B Cell Origin of Pancreatic Cell Derived iPS Cells In order to evaluate the differentiation potential of iPS cells derived from human beta cells, the present inventors utilized two recently-developed genetic lineage tracing approaches [Russ et al., Diabetes 57, 1575-1583 (2008); Russ et al., PLoS One 4, e6417 (2009)] (FIG. 1A) to specifically label human beta cells within cultures of pancreatic islet cells containing multiple cell types (FIG. 1B). Both labeling approaches are based on the Cre/lox system, routinely used in transgenic animals. In the present procedure, the human islet cells were infected with a mixture of two lentiviral vectors. In the first system, Cre recombinase was expressed under control of the insulin promoter, while the second system was improved by fusing Cre recombinase to the estrogen receptor (ER), rendering DNA recombination inducible by tamoxifen. Since the insulin promoter is expressed only in beta cells, the Cre enzyme excises the floxed DNA region of the reporter constructs, thereby activating constitutive GFP expression specifically in beta cells (FIGS. 1A and 1B). The genetic label is stable in all beta-cell-derived (BCD) progeny, making it possible to determine the cellular origin of reprogrammed cells derived from beta cells.

Figure 3B:
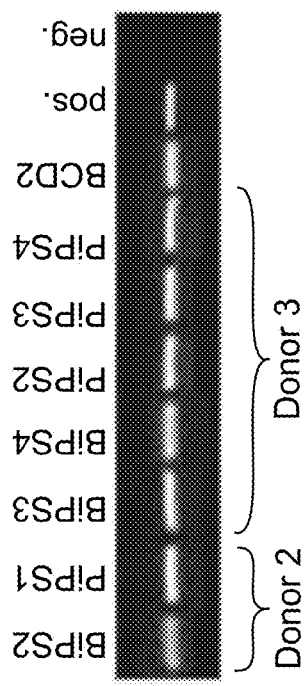
Figure 3A:
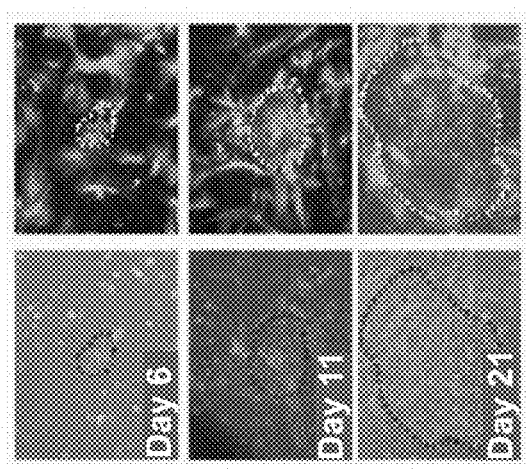
Figure 3C:
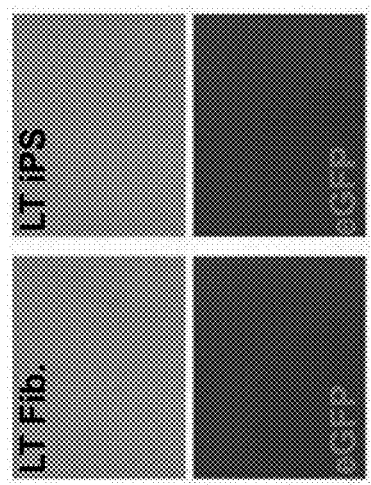
Figure 3G:
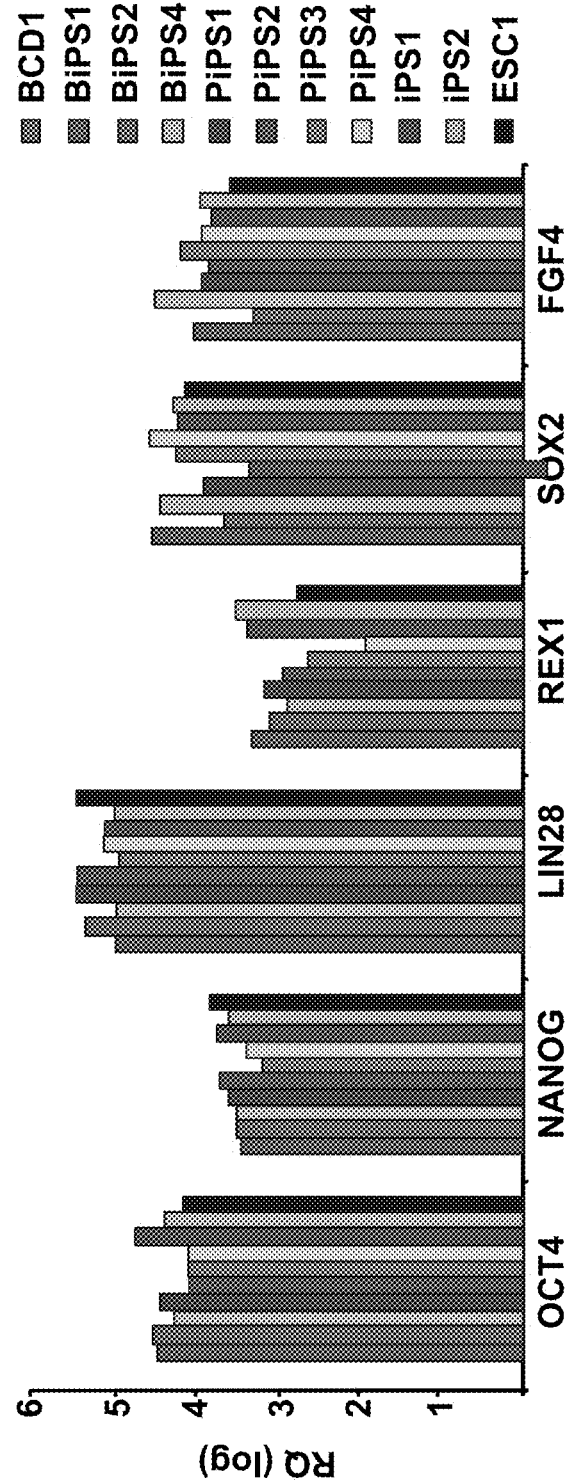

BCD cells undergo de-differentiation and epithelial to mesenchymal transition following their growth in culture, as was described previously [Russ et al., Diabetes 57, 1575-1583 (2008); Russ et al., PLoS One 4, e6417 (2009)]. Human islet-cell cultures containing about 20% lineage-traced BCD cells following 3-9 weeks in culture were transduced with retroviral vectors encoding the four pluripotency-inducing factors OCT4, SOX2, KLF4 and cMYC. ES-like colonies were detected 3-6 weeks later with an extremely low efficiency (0.0001%) (FIG. 3A). A number of these colonies were isolated and expanded for further analysis. To demonstrate the beta-cell origin of the iPS cells, DNA PCR analysis of the integrated recombed reporter cassettes was performed. Out of dozens of iPS cell lines established from 4 islet donors, 4 cell lines containing only the shorter PCR product corresponding to the recombined reporter gene (FIG. 1C), were identified as true beta-cell-derived induced pluripotent stem (BiPS) cells. 4 isogenic non-beta pancreatic iPS (PiPS) cell lines derived from non-beta cells of the same donors were also obtained, as judged by the absence of a recombined reporter gene (FIG. 1C, FIG. 3B) (in spite of the presence of DNA of the Cre gene from the 2 labeling vectors). When foreskin fibroblasts were infected with the genetic lineage-tracing system, no DNA recombination of the reporter vector or GFP expression were observed, further indicating the specificity of the labeling system (FIGS. 3C, 3D and 3E). Transduction of the lineage traced fibroblasts with the pluripotency-inducing factors resulted in establishment of iPS cell colonies at a normal efficiency. However, no GFP expression or recombination event could be detected following reprogramming, indicating that the labeling system was not affected by the reprogramming process (FIGS. 3C, 3D).

Example 2

Characterization of BiPS Cells

The BiPS cell lines contained all 4 retroviral transgenes, as judged by genomic DNA PCR analyses (FIG. 3E). BiPS cell lines showed a typical ES-like morphology (FIG. 3F), and could be maintained for at least 30 passages.

Figure 3H:
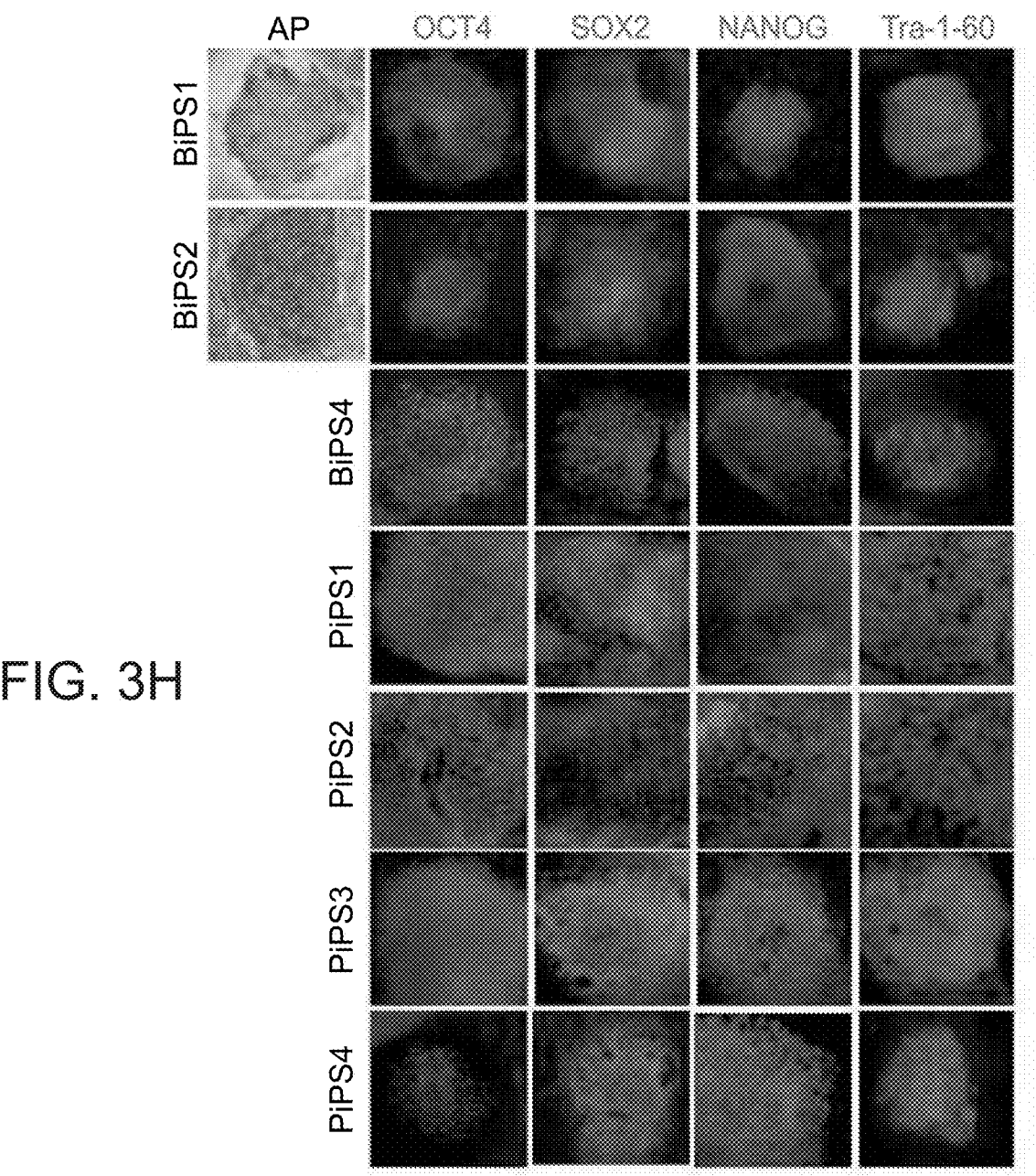
Figure 3I:
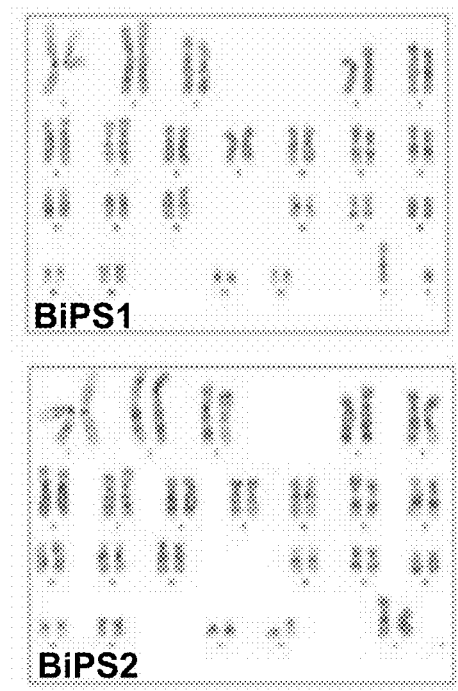
Figure 4F:
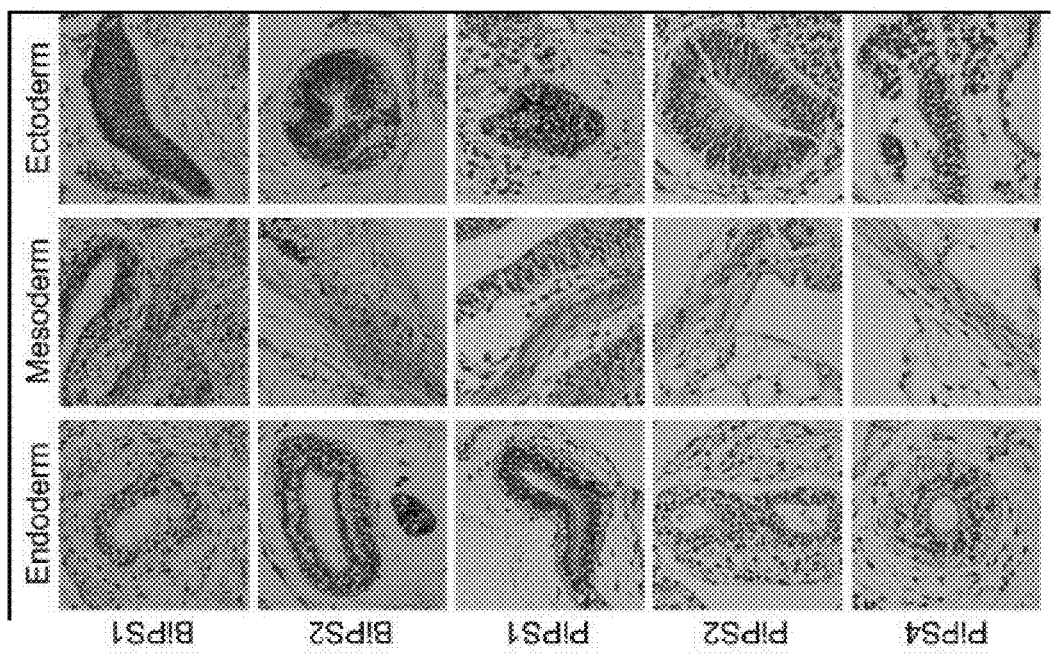

BiPS cell clones were characterized using stringent criteria for pluripotency of human iPS cells [Maherali, N. & Hochedlinger, K. Cell Stem Cell 3, 595-605 (2008); Daley, G. Q. et al. Cell Stem Cell 4, 198-199 (2009)]. Thus, BiPS cells were positive for many pluripotency markers at both RNA and protein levels, silenced the retroviral transgenes, and maintained a normal diploid karyotype (FIG. 3F, 3G, 3H, 3I). It has recently been shown (Chan et al., Nat. Biotechnol. 11, 1033-1037 (2009)) that bona fide iPS cells can be distinguished from partially-reprogrammed cells by the expression of REX1, DNMT3B and Tra-1-60. BiPS cells express these markers in comparable levels to other human iPS and ES cells, confirming their full reprogramming (FIGS. 3H, 3I, 4A). In addition, microarray analysis of gene expression showed that BiPS cells were globally similar to human iPS or ES cells, as shown by scatter plot and hierarchical cluster analyses, while differing markedly from the parental BCD cells (FIGS. 4B, 4C). Of note, the linear correlation coefficient between BiPS1 and ES cells was 0.94, similar to the correlation coefficient between two different ES cell lines ($R^2=0.94$), and different from the correlation coefficient between BiPS1 and its original somatic cell lines ($R^2=0.65$). BiPS cells gave rise to differentiated cells from the three embryonic germ layers in vitro, as judged by EB formation assay, and in vivo, as evidenced by teratoma formation assay (FIGS. 4D, 4E, 4F). Taken together, these results demonstrate that BiPS cells are truly reprogrammed pluripotent stem cells.

Example 3

Differentiation of BiPS Cells

Levels of histone H3 acetylation, a hallmark of open chromatin structure, were evaluated by chromatin immunoprecipitation (ChIP) in fresh human islets, BCD, BiPS, PiPS, iPS derived from fibroblasts, and ES cells. Although BCD cells do not express insulin or the beta-cell transcription factors PDX1 and MAFA (FIG. 1D), they maintain a partially open chromatin structure on the promoter regions of these genes, as judged by histone H3 acetylation (FIG. 1E). This epigenetic imprint was also maintained in the insulin and PDX1 gene promoters in 3 BiPS cell lines in levels comparable to those of BCD cells, while not detected in PiPS, iPS or ES cells of similar passage numbers (FIG. 1F). In contrast, the histone H3 on the MAFA promoter underwent deacetylation during reprogramming of BCD cells into BiPS cells (FIG. 1G). To determine whether a similar preservation of epigenetic memory occurred at the DNA methylation level, Illumina's Infinium HumanMethylation27 BeadChiP arrays were used to compare the DNA methylation patterns of BCD, BiPS, fibroblast, iPS and ES cells. Hierarchical clustering revealed a unique DNA methylation pattern in BiPS cells that considerably distinguished them from BCD cells, and also separated them from other pluripotent stem cells (FIG. 1I). A closer look at the DNA methylation status of specific genes revealed that pluripotency related genes have undergone demethylation during reprogramming, while somatic-specific genes became more methylated (FIG. 1H). Genes expressed in human islet cells which were hypomethylated in BCD cells, and remained hypomethylated in BiPS cells were also detected, while being methylated in fibroblasts, fibroblast-derived iPS, and ES cells (FIG. 1H). These findings support the retention of an epigenetic memory in BiPS cells. Finally, methylation of the PDX1 promoter was compared in BiPS, and iPS cells by pyrosequencing analysis. BiPS cells exhibited significantly lower DNA methylation levels, characteristic of transcribed genes, in 8/13 positions analyzed, compared with iPS derived from fibroblasts cells (FIG. 1J), and PiPS cells derived from non-beta pancreatic cells which exhibited about 25% higher DNA methylation levels than BiPS cells. The higher DNA methylation levels in the PDX1 promoter in iPS cells, compared with BiPS cells may reflect a variable epigenetic memory in iPS cells derived from fibroblasts.

To address the possibility that the observed epigenetic memory rendered BiPS cells permissive to skewed differentiation into cells of the endodermal lineage, and possibly into insulin-producing cells, expression of beta-cell genes was analyzed in EBs and teratomas derived from BiPS cell lines, in comparison to PiPS, iPS, and ES cells. Multiple differentiation experiments, performed at similar passage numbers showed that insulin, PDX1 and FOXA2 mRNA expression was significantly higher in both EBs and teratomas derived from BiPS cells, when compared to EBs and teratomas derived from PiPS, iPS, and ES cells (FIG. 2A, 2B). Although both EBs and teratomas are comprised of many different cell types, which may hinder the conclusions drawn from their analysis, the present data does show preferred differentiation into endoderm in these complex differentiated structures. No significant differences were noted between the 4 BiPS cell lines studied. Moreover, C-peptide protein could only be detected in EBs derived from BiPS cells (FIG. 2C). However, C-peptide protein was not detectable in teratomas derived from either BiPS or ES cells (data not shown). In contrast to PDX1, MAFA expression in EBs from BiPS cells was not significantly different from that in iPS and ES cells (data not shown), in accordance with the lack of epigenetic memory in the MAFA promoter (FIG. 1G). Unlike the beta-cell genes, no significant differences were found in genes of ectodermal, mesodermal, and endodermal tissues (data not shown).

Figure 4G:
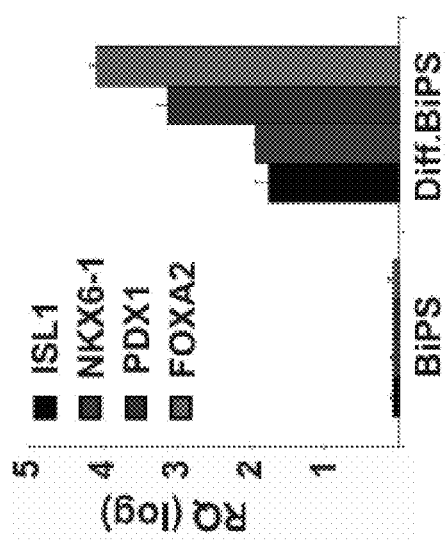
Figure 4H:
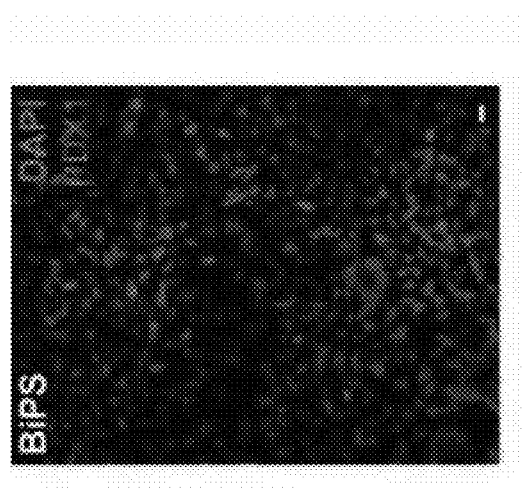

Next a protocol for induced differentiation of human ES cells into pancreatic endocrine progenitors was used [Kroon et al., Nat. Biotechnol. 26, 443-452 (2008)]. BiPS cells could be differentiated into endocrine progenitor cells expressing the beta-cell transcription factors PDX1, NKX6.1, FOXA2 and ISL1 by day 12 (FIGS. 4G, 4H). Previously, it was shown that pancreatic endocrine progenitors can further mature into beta-like cells when grafted into mice [Kroon et al., Nat. Biotechnol. 26, 443-452 (2008)]. The present inventors thus transplanted 2.5-4×10⁶ BiPS or ES cell-derived pancreatic endocrine progenitors under the renal capsule of SCID mice and measured serum levels of human C-peptide following glucose challenge. Transplantation of BiPS cell-derived pancreatic endocrine progenitor cells resulted in detectable serum levels of human C-peptide as early as 3 weeks post-transplantation, while no human C-peptide was detected in mice transplanted with human ES cell-derived pancreatic endocrine progenitors during the first 4 weeks following transplantation (FIG. 2D). Human C-peptide was detected in the ES cell-derived progenitors 6 weeks following transplantation, however, these C-peptide levels were an order of magnitude lower than in BiPS cell-derived grafts. The levels of C-peptide detected in BiPS derived grafts after 3-4 weeks suggest that BiPS cell-derived endocrine progenitor cells matured faster in vivo, compared to ES cell-derived endocrine progenitor cells. Graft analysis 6-7 weeks post-transplantation revealed insulin mRNA expression in all three BiPS cell-derived grafts examined (FIG. 2E). C-peptide staining was detected in 2/7 BiPS cell-derived grafts at this time point (FIG. 2F). These grafts also expressed glucagon, somatostatin, pancreatic polypeptide, and amylase transcripts (FIG. 2E). In contrast, ES cell-derived grafts expressed detectable levels of the other four pancreatic transcripts analyzed, but not insulin (FIG. 2E).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating insulin producing cells, comprising:
   (a) expanding human pancreatic beta cells so as to generate dedifferentiated cells which express a lower amount of insulin or PDX-1 than differentiated pancreatic beta cells as assayed by Immunohistochemistry or RT-PCR; and subsequently
   (b) generating induced pluripotent stem (iPS) cells from said dedifferentiated cells by expressing OCT4, SOX2, KOF4 and cMYC, wherein said iPS cells have an open chromatin structure in either the PDX-1 or insulin promoter; and
   (c) differentiating said induced pluripotent stem cells into insulin producing cells.

2. The method of claim 1, wherein said expanding is effected in a medium comprising CMRL-1066.

3. The method of claim 2, wherein said expanding is effected for 3-16 weeks.

4. The method of claim 1, wherein said human pancreatic beta cells are a homogeneous population of human pancreatic beta cells.

5. The method of claim 1, wherein said human pancreatic beta cells are comprised in a mixed population of pancreatic cells.

6. The method of claim 5, further comprising selecting said iPS cells that have an open chromatin structure in insulin or PDX-1 promoter following step (b) and prior to step (c).

7. The method of claim 6, wherein said selecting is effected by analyzing a chromatin structure of a promoter of an insulin or PDX-1 gene in said iPS cells, and based on said analyzing, selecting cells which have an open chromatin structure of said promoter.

8. The method of claim 1, wherein said differentiating said induced pluripotent stem cells towards a pancreatic lineage is effected by differentiating said induced pluripotent stem cells into definitive endoderm and subsequently differentiating said definitive endoderm cells into pancreatic progenitor cells.

9. A method of generating insulin producing cells, comprising:
   (a) generating induced pluripotent stem (iPS) cells from human pancreatic beta cells by expressing OCT4, SOX2, KOF4 and cMYC, wherein said iPS cells have an open chromatin structure in either the PDX-1 or insulin promoters; and
   (b) differentiating said induced pluripotent stem cells into insulin producing cells.

10. The method of claim 9, further comprising selecting said iPS cells that have an open chromatin structure in either the insulin or PDX-1 promoters following step (a) and prior to step (b).

11. The method of claim 9 wherein said human pancreatic beta cells have been expanded in CMRL-1066 prior to step (a) to generate dedifferentiated human pancreateic beta cells which express a lower amount of insulin or PDX-1 than differentiated pancreatic beta cells as assayed by Immunohistochemistry or RT-PCR.

12. A method of generating insulin producing cells, comprising:
   (a) generating induced pluripotent stem (iPS) cells from human pancreatic beta cells by expressing OCT4, SOX2, KOF4 and cMYC, wherein said iPS cells have an open chromatin structure in either the PDX-1 or insulin promoters;
   (b) selecting said iPS cells that have an open chromatin structure in either the insulin or PDX-1 promoters; and
   (c) differentiating said iPS cells that were selected in step (b) into insulin producing cells.

13. The method of claim 12 wherein said human pancreatic beta cells have been expanded in CMRL-1066 prior to step (a) to generate dedifferentiated human pancreateic beta cells which express a lower amount of insulin or PDX-1 than differentiated pancreatic beta cells as assayed by Immunohistochemistry or RT-PCR.

* * * * *

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gagacaatgt cccctgctgt                                              20

<210> SEQ ID NO 2
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 2
cctggacttt gctgtttgt                                               19

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
atccacgctg ttttgacctg                                              20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
aagtcgtgct gcttcatgtg                                              20
```

```
<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
tgtgagcagg gacaggtctg                                              20

<210> SEQ ID NO 6
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 6
tcctcaggac cagcggg                                                 17

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tcagaagagg ccatcaagca                                              20

<210> SEQ ID NO 8
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 8
gtccagccac cctggaatc                                               19

<210> SEQ ID NO 9
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 9
cagctggaga actactgcaa ctaga                                        25

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
gctggttcaa gggctttatt cc                                           22

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 11
agagtcgtca agggtctgga                                               20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
cggaacgtag cttcccaata                                               20

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
cctcttccca cagctgtttc                                               20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
cttatcccca tggcaactca                                               20

<210> SEQ ID NO 15
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 15
ccgtggtacc aaagctga                                                 18

<210> SEQ ID NO 16
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 16
agccggctgg ggtagaag                                                 18

<210> SEQ ID NO 17
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 17
gggaaatggg aggggtgcaa aagagg                                        26

<210> SEQ ID NO 18
<211> LENGTH: 26

```
<212> TYPE: DNA
<213> ORGANISM: Artificial sequence
<220> FEATURE:
<223> OTHER INFORMATION: Single strand DNA oligonucleotide

<400> SEQUENCE: 18
ttgcgtgagt gtggatggga ttggtg                                          26

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 19
catgagtgtg gatccagctt g                                               21

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
cctgaataag cagatccatg g                                               21

<210> SEQ ID NO 21
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 21
tcacagtcca gcaggtgttt g                                               21

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
tcttgtcttt gcccgtttct                                                 20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
agccacatcg ctcagacacc                                                 20

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
```
gtactcagcg gccagcatcg                                                    20

<210> SEQ ID NO 25
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 25
ccccagggcc ccattttggt acc                                                23

<210> SEQ ID NO 26
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 26 cccttttttct ggagactaaa taaa                                              24

<210> SEQ ID NO 27
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 27
ggcacccctg gcatggctct tggctc                                             26

<210> SEQ ID NO 28
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 28
ttatcgtcga ccactgtgct gctg                                               24

<210> SEQ ID NO 29
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 29
acgatcgtgg ccccggaaaa ggacc                                              25

<210> SEQ ID NO 30
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 30
ccctttttct ggagactaaa taaa                                               24

<210> SEQ ID NO 31
<211> LENGTH: 27
<212> TYPE: DNA
<213> ORGANISM: Artificial sequence

```
<220> FEATURE:
<223> OTHER INFORMATION: Single strand DNA oligonucleotide

<400> SEQUENCE: 31
caacaaccga aaatgcacca gccccag                                           27

<210> SEQ ID NO 32
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 32 cccttttct ggagactaaa taaa                                               24
```